United States Patent [19]

Greve

[11] Patent Number: 4,634,764
[45] Date of Patent: Jan. 6, 1987

[54] NON-AZO AND AZO COMPOUNDS CONTAINING AT LEAST ONE 4,6-DIAMINO-1-SUBSTITUTED-5-SUBSTITUTED CARBAMOYLPYRID-2-ONE GROUP

[75] Inventor: Manfred Greve, Dornach, Switzerland

[73] Assignee: Sandoz Ltd., Basel, Switzerland

[21] Appl. No.: 550,954

[22] Filed: Nov. 10, 1983

[30] Foreign Application Priority Data

Nov. 22, 1982 [DE] Fed. Rep. of Germany ....... 3243092

[51] Int. Cl.[4] .................. C09B 29/42; C09B 31/153; C09B 31/28; C09B 44/08

[52] U.S. Cl. .................................. 534/759; 534/606; 534/608; 534/609; 534/740; 534/744; 534/754; 534/755; 534/756; 534/760; 534/763; 534/771; 544/107; 544/360; 546/193; 546/194; 546/268; 546/275; 546/290; 546/297

[58] Field of Search ............... 534/606, 608, 756, 771, 534/609, 740, 744, 760, 763, 754, 758; 546/193, 194, 268, 275, 290, 297; 544/107, 360

[56] References Cited

U.S. PATENT DOCUMENTS

| | | | |
|---|---|---|---|
| 3,852,261 | 12/1974 | Steinemann | 260/156 |
| 3,869,441 | 3/1975 | Hughes | 260/156 |
| 3,899,478 | 8/1975 | Fleckbustein et al. | 534/608 |
| 4,065,254 | 12/1977 | Buhler et al. | 8/1 |
| 4,087,244 | 5/1978 | Greve et al. | 8/41 |

FOREIGN PATENT DOCUMENTS

| | | | |
|---|---|---|---|
| 41040 | 12/1981 | European Pat. Off. | 534/606 |
| 92520 | 10/1983 | European Pat. Off. | 534/606 |
| 2190972 | 2/1974 | France | 260/153 |
| 1296857 | 11/1972 | United Kingdom | 260/156 |
| 1550830 | 11/1976 | United Kingdom | 260/156 |

*Primary Examiner*—Floyd D. Higel
*Attorney, Agent, or Firm*—Gerald D. Sharkin; Richard E. Vila; Melvyn M. Kassenoff

[57] ABSTRACT

Compounds of the formula

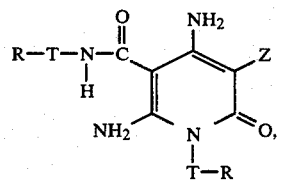

wherein
each R is independently $-N(R_1)_2$, $-N^{\oplus}(R_2)_3$ $A^{\ominus}$ or hydroxy, wherein
each $R_1$ is independently hydrogen, alkyl, substituted alkyl, cycloalkyl, substituted cycloalkyl or aryl or
both $R_1$'s taken together and with the nitrogen atom to which they are attached form a 5- or 6-membered saturated heterocyclic ring,
each $R_2$ is independently alkyl, substituted alkyl, cycloalkyl, substituted cycloalkyl or aryl or
two $R_2$'s taken together and with the nitrogen atom to which they are attached form a 5- or 6-membered saturated heterocyclic ring or
all three $R_2$'s taken together and with the nitrogen atom to which they are attached form a 5- or 6-membered unsaturated heterocyclic ring, and
$A^{\ominus}$ is a non-chromophoric anion,
each T is independently a bridging radical, and
Z is hydrogen or $-N=N-D$, wherein D is a diazo component radical,
are dyes useful for the dyeing of for example, paper, leather, cellulosic materials such as cotton and textiles comprising polyacrylonitrile or polyamides or polyesters modified to contain anionic groups. Polymeric compounds containing at least two units each of which contains residues of two compounds of said formula, which may be the same or different, joined by biscationic bridging radicals are also useful as dyes for the same materials.

12 Claims, No Drawings

NON-AZO AND AZO COMPOUNDS CONTAINING AT LEAST ONE 4,6-DIAMINO-1-SUBSTITUTED-5-SUBSTITUTED CARBAMOYLPYRID-2-ONE GROUP

According to the invention there is provided compounds of formula I

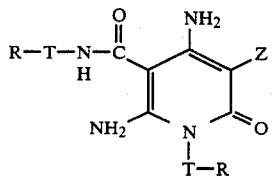

in which

Z is hydrogen or —N═N—D where D is the residue of a diazo component;

each T independently is a bridging group;

each R independently is —N(R$_1$)$_2$, —N$^\oplus$(R$_2$)$_3$A$^\ominus$ or —OH;

where each R$_1$ independently is hydrogen; alkyl; alkyl substituted by halogen, cyano, hydroxy, phenyl or carbamoyl; cycloalkyl; cycloalkyl substituted by 1 to 3 C$_{1-4}$alkyl groups or aryl;

and each R$_2$ independently is alkyl; alkyl substituted by halogen, cyano, hydroxy, phenyl or carbamoyl; cycloalkyl; cycloalkyl substituted by 1 to 3 C$_{1-4}$alkyl groups or aryl;

or both R$_1$'s or two R$_2$'s together with the N-atom to which they are attached form a 5- or 6-membered saturated heterocyclic ring;

or all three R$_2$'s together with the N-atom to which they are attached form a 5- or 6-membered unsaturated heterocyclic ring, and A$^\ominus$ is a non-chromophoric anion.

Preferably Z is Z' where Z' is defined later.

Preferred compounds of formula I are of formula II

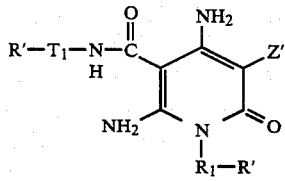

in which

T$_1$ is C$_{1-12}$alkylene which may be interrupted by 1 to 3 heteroatoms or C$_{3-12}$alkenylene group which may be interrupted by 1 to 3 heteroatoms;

R' is

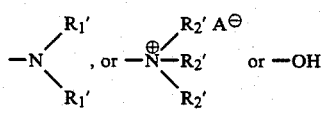

where each R$_1$' independently is hydrogen; C$_{1-12}$alkyl unsubstituted or substituted by halogen, cyano, hydroxy, unsubstituted phenyl CONH$_2$; phenyl unsubstituted or substituted by 1 to 3 C$_{1-4}$alkyl groups or cyclohexyl unsubstituted or substituted by 1 to 3 C$_{1-4}$alkyl groups; or both R$_1$'s together with the N-atom to which they are attached form an unsubstituted piperidine, unsubstituted morpholine, unsubstituted piperazine, C- unsubstituted N-C$_{1-4}$alkylpiperazine or unsubstituted pyrrolidine ring; and each R$_2$' independently, is C$_{1-12}$alkyl unsubstituted or substituted by halogen, cyano, hydroxy, unsubstituted phenyl or —CONH$_2$; phenyl unsubstituted or substituted by 1 to 3 C$_{1-4}$alkyl groups or cyclohexyl unsubstituted or substituted by 1 to 3 C$_{1-4}$alkyl groups; or two R$_2$'s together with the N-atom to which they are attached form a C-unsubstituted piperidine, C-unsubstituted morpholine, C-unsubstituted piperazine or C-unsubstituted pyrrolidine, all three R$_2$'s together with the N-atom to which they are attached form a pyridinium ring unsubstituted or substituted by 1 to 3 C$_{1-4}$alkyl groups; or

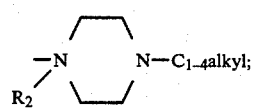

and

Z' is hydrogen,

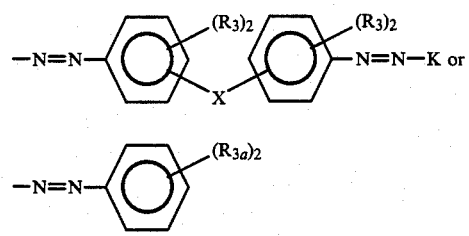

where each R$_3$ independently is halogen, C$_{1-4}$alkyl, C$_{1-4}$alkoxy or hydrogen; and each R$_{3a}$ independently has a significance of R$_3$ (independent of R$_3$) or —NO$_2$,

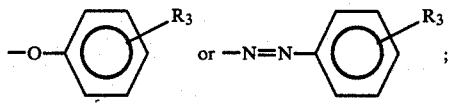

X when all R$_3$'s are hydrogen is selected from X$_1$ to X$_{76}$ where X$_1$ is a direct bond;

X$_2$ is a linear or branched C$_{1-4}$alkylene group;

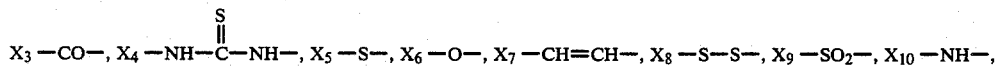

-continued
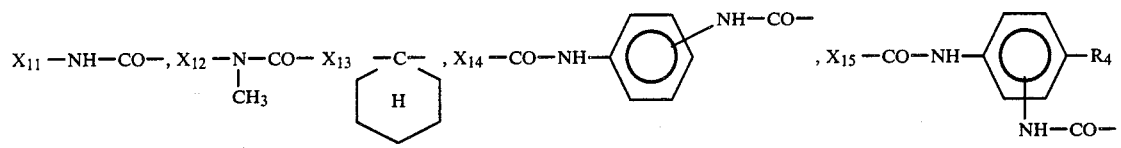
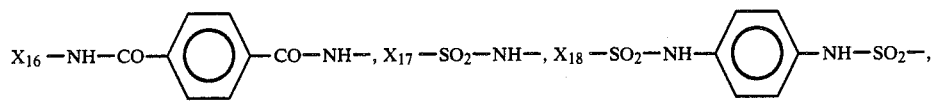
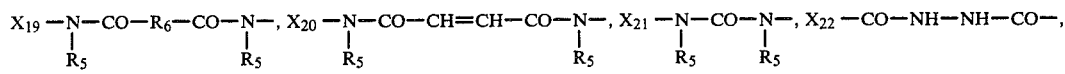
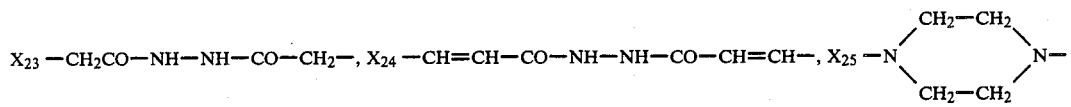
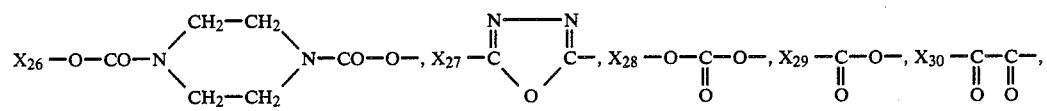
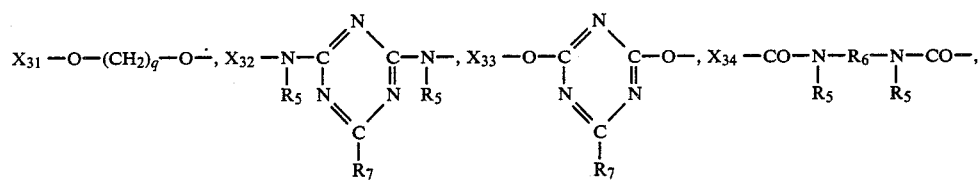
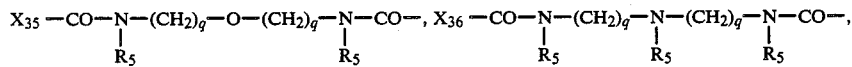
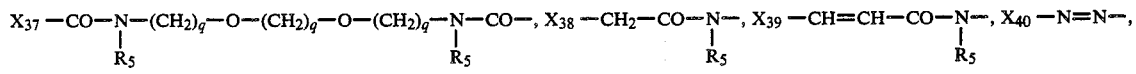
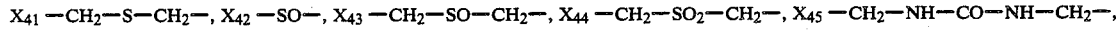
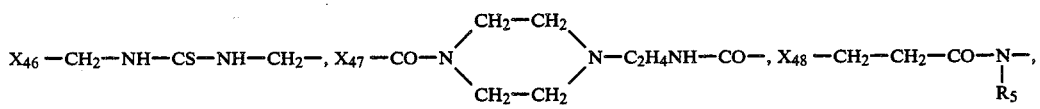
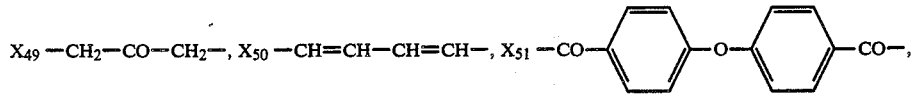
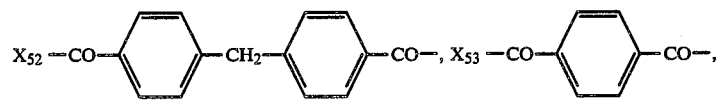
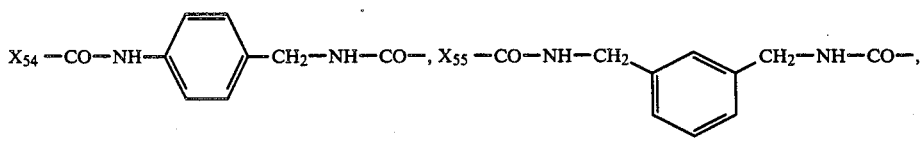

-continued

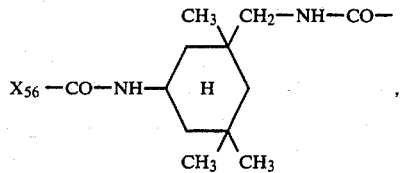, 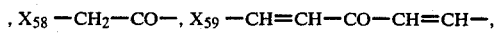

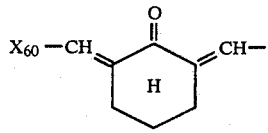, 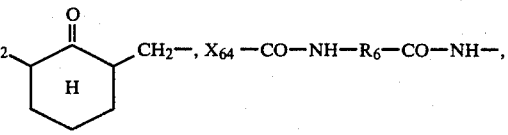

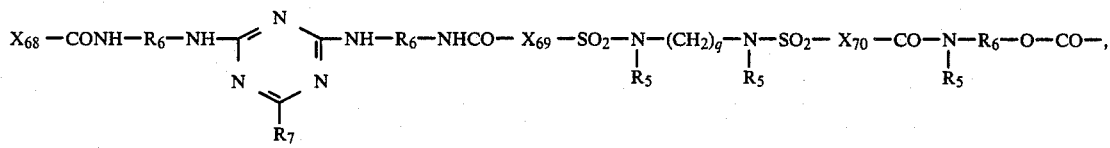

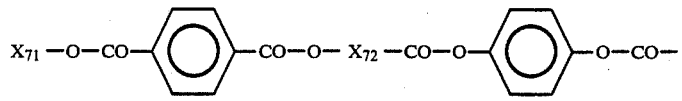

$X_{68}$ —CONH—$R_6$—NH— 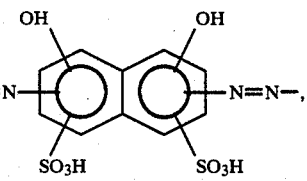 —NH—$R_6$—NHCO— $X_{69}$ —SO$_2$—N(R$_5$)—(CH$_2$)$_q$—N(R$_5$)—SO$_2$— $X_{70}$ —CO—N(R$_5$)—$R_6$—O—CO—,

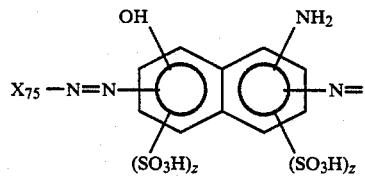

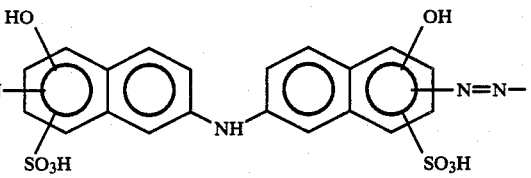

each z independently is 0, 1 or 2;
each $R_4$ independently is halogen, unsubstituted $C_{1-4}$alkyl or unsubstituted $C_{1-4}$alkoxy;
each $R_5$ independently is hydrogen or unsubstituted $C_{1-4}$alkyl;
each $R_6$ independently is a linear or branched unsubstituted $C_{1-4}$alkylene group;
each $R_7$ independently is —NH$_2$, —OH, —NH—CH$_2$CH$_2$OH, —NH(CH$_2$)$_3$—N(CH$_3$)$_2$, —N(CH$_2$—CH$_2$—OH)$_2$, —N(CH$_3$)$_2$, —N(C$_2$H$_5$)$_2$, halogen, —NH—(CH$_2$)$_3$—N(C$_2$H$_5$)$_2$,

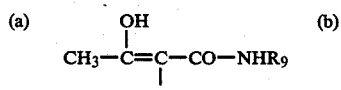

each q independently is 1, 2, 3 or 4;
or X when one or more $R_3$'s is or are other than hydrogen, is selected from $X_1$, $X_2$, $X_{14}$, $X_{21}$, $X_{32}$ and $X_{34}$;
K is a group of the formula (a) 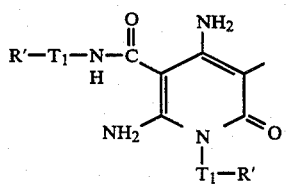

(b) $CH_3-\underset{\underset{|}{OH}}{C}=C-CO-NHR_9$

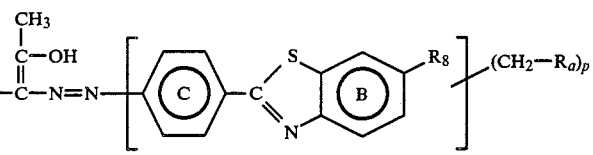

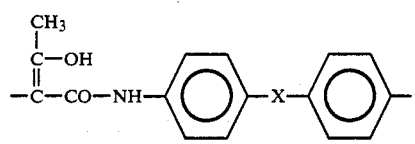

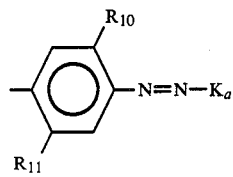 (d)

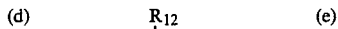 (e)

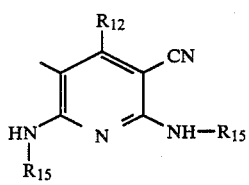 (f)

 (g)

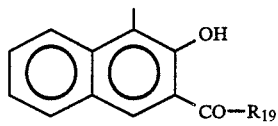 (h)

 (i)

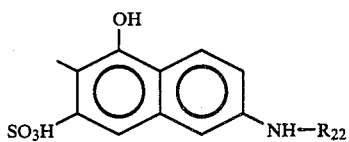 (k)

 (l)

where
$R_a$ is a significance of R' other than —OH;
each $R_8$ independently is hydrogen, methyl, methoxy or ethoxy;
$R_9$ is a group of the formula

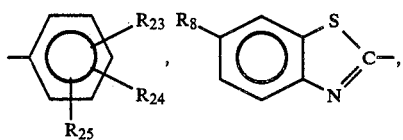

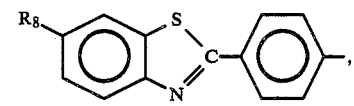

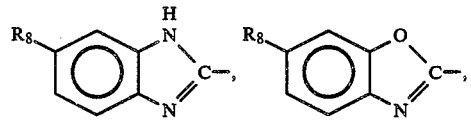

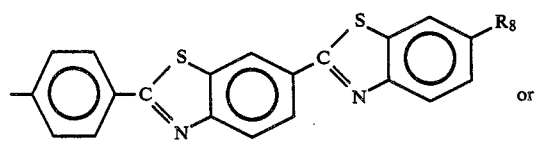 or

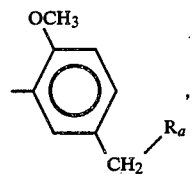

where
$R_a$ is defined above;
$R_{10}$ and $R_{11}$ independently of each another are selected from unsubstituted $C_{1-4}$alkyl and unsubstituted $C_{1-4}$alkoxy;
$R_{12}$ is hydrogen, unsubstituted $C_{1-4}$alkyl, unsubstituted benzyl or unsubstituted phenyl;
$R_{13}$ is H, —CN, —CONH$_2$,

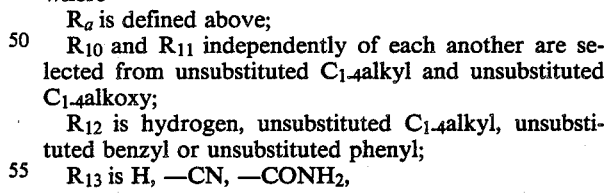

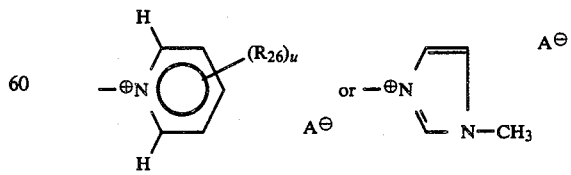

$R_{14}$ is hydrogen, $C_{1-4}$alkyl unsubstituted or substituted by one unsubstituted phenyl group, —(CH$_2$)$_2$—CN, —(CH$_2$)$_2$OH, —(CH$_2$)$_r$—N(R$_{1a}$)$_2$, —(CH$_2$)$_3$—OCH$_3$,

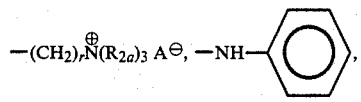

where
$R_{1a}$ has all the significances of $R_1$ (including the cyclic significances) except hydrogen and $R_{2a}$ has all the significances of $R_2$ (including the cyclic significances).

r is 2, 3, 4, 5 or 6;

each $R_{15}$ independently is hydrogen, unsubstituted $C_{1-4}$alkyl, —(CH$_2$)$_3$—OCH$_3$, —(CH$_2$)$_2$—OH, —(CH$_2$)$_3$—N(CH$_3$)$_2$, —(CH$_2$)$_3$N$^\oplus$(CH$_3$)$_3$A$^\ominus$ or —(CH$_2$)$_3$—N(C$_2$H$_5$)$_2$;

$R_{16}$ is —OH or —NH$_2$;

$R_{17}$ is unsubstituted $C_{1-4}$alkyl or —CO—$R_{27}$;

$R_{18}$ is

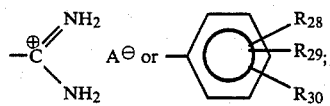

$R_{19}$ is —NH—NH$_2$,

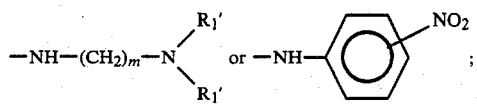

$R_{20}$ is an unsubstituted $C_{1-4}$alkyl group,

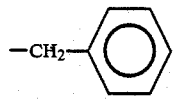

or —(CH$_2$)$_2$CN;

$R_{21}$ is an unsubstituted $C_{1-4}$alkyl group, —(CH$_2$)$_m$—N$^\oplus$(CH$_3$)$_3$A$^\ominus$ or

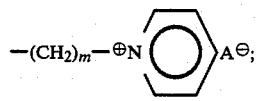

$R_{22}$ is

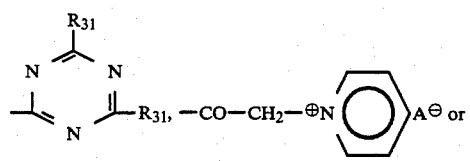

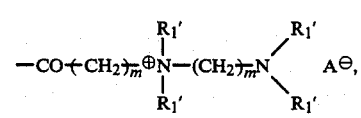

$R_{23}$, $R_{24}$ and $R_{25}$ independently of one another are selected from hydrogen, halogen, unsubstituted $C_{1-4}$alkyl, unsubstituted $C_{1-4}$alkoxy, —NO$_2$ and —CN;

$R_{26}$ is unsubstituted $C_{1-4}$alkyl, —CON[(C$_{1-4}$)alkyl)]$_2$, —N(C$_{1-4}$alkyl)$_2$, —CONH(C$_{1-4}$alkyl), —NH(C$_{1-4}$alkyl) or —NH$_2$;

u is 0, 1, or 2;

$R_{27}$ is —O—$R_{32}$ or

$R_{28}$ and $R_{29}$ independently of each another are hydrogen, halogen, unsubstituted $C_{1-4}$alkyl; unsubstituted $C_{1-4}$alkoxy, —NO$_2$, —NH$_2$ or —NHCOCH$_3$;

$R_{30}$ is hydrogen or —NH—CO—(CH$_2$)$_m$—$R_{35}$;

each $R_{31}$ independently is —NH—(CH$_2$)$_m$—N(R$_1'$)$_2$;

$R_{32}$ is $C_{1-4}$alkyl;

$R_{33}$ and $R_{34}$ independently are hydrogen or unsubstituted $C_{1-4}$alkyl;

$R_{35}$ is —N$^\oplus$(R$_2'$)$_3$A$^\ominus$ or

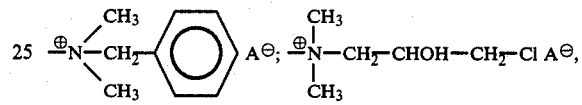

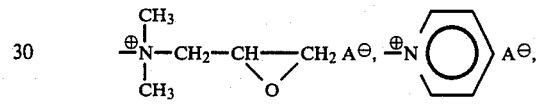

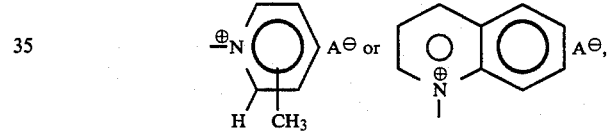

p is a number from 1 to 3 inclusive;

each m independently is 1, 2, 3, 4, 5 or 6; and $K_a$ is a coupling component of the acetoacetyl-alkyl or arylamide series, the pyridone series, the diaminopyridine series, the pyrazolone series, the aminopurazole series, the α- or β-naphthol series, the aminophenyl series or the barbituric acid series;

$K_a$ is preferably a group of formulae (a), (b), (c) and (e) to (k) above (defined under symbol K).

Preferred compounds of formula II are of formula III

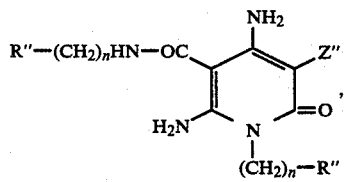

where R'' is —OH or

and Z'' is hydrogen,

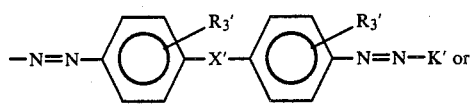 or

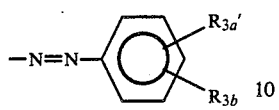

where
R₃' is hydrogen, methyl, methoxy or chloro;
R₃ₐ' is hydrogen, Cl, —NO₂,

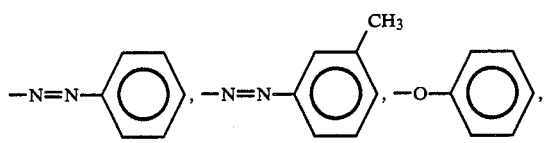,

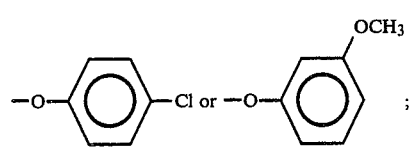;

R₃ᵦ is hydrogen, Cl, —NO₂ or CH₃;
X', when each R₃' is hydrogen is selected from X₁, X₅, X₆, X₇, X₁₀, X₁₁, X₁₂, X₁₆, X₁₇, X₂₂, X₂₅, X₂₆, X₂₇, X₃₀, X₃₁, X₄₉, X₅₀, X₅₁, X₅₂, X₅₃, X₅₄, X₅₈, X₅₉, X₆₄; or X₂' to X₃₄^vi below:

| | |
|---|---|
| X₂' | —CH₂—, |
| X₂'' | —(CH₂)₂—, |
| X₂''' | —(CH₂)₃—, |
| X₂^iv | —(CH₂)₄—, |

X₁₄'  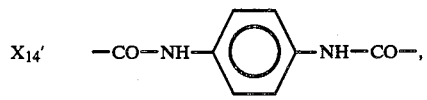

X₁₅'  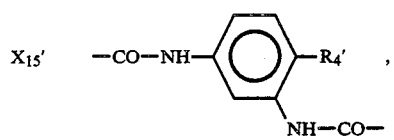

X₁₉'  —NH—CO—CH₂CH₂—CO—NH—,

X₁₉''  —NH—CO—(CH₂)₄—CO—NH—,

X₁₉'''  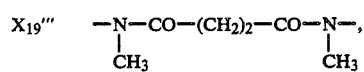

X₂₀'  —NH—CO—CH=CH—CONH—,

X₂₀''  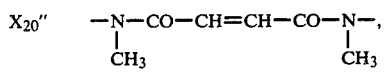

X₂₁'  —NHCONH—,

X₂₁''  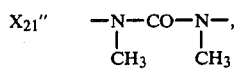

X₃₂'  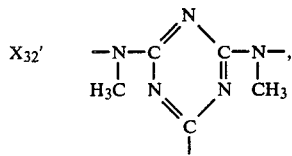

X₃₂''  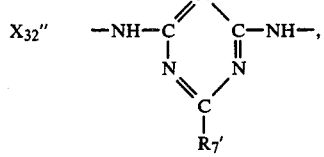

X₃₄'   —CO—NH—(CH₂)₂—NH—CO—,

X₃₄''  —CO—NH—(CH₂)₃—NH—CO—,

X₃₄''' —CO—NH—(CH₂)₄—NH—CO—,

X₃₄^iv  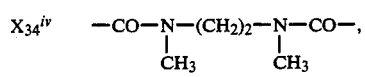

X₃₄^v  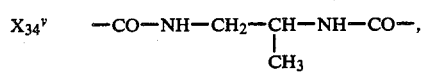

X₃₄^vi 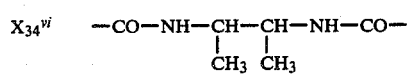

or X', when one or more R₃' is other than hydrogen is X₁, X₂₁', X₁₄', X₃₂'', X₂', X₂'' or X₃₄';
each R₄' independently is hydrogen, chlorine, methyl or methoxy;
each R₇' independently is Cl, —NH—CH₂CH₂OH, —N(CH₂CH₂OH)₂, —OH, —NH₂, —NH(CH₂)₃N(C₂H₅)₂,

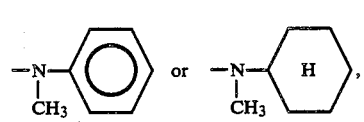, n is an integer from 2 to 6 inclusive;
each R₁'' is hydrogen or unsubstituted, linear or branched C₁₋₄alkyl;
K' is a group of one of the formula a₁ to k₁ below:

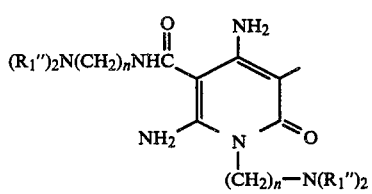 (a₁)

$$CH_3-\underset{\underset{|}{}}{C}=\underset{|}{C}-CONH-R_9'$$
OH (b₁)

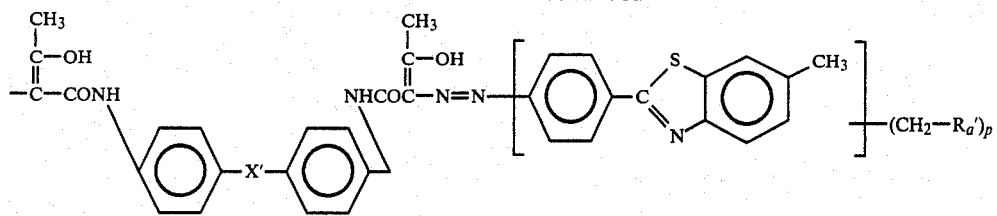 (c₁)
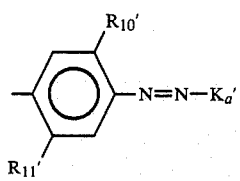 (d₁)
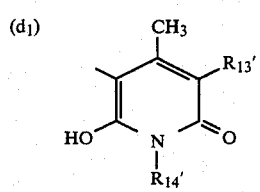 (e₁)
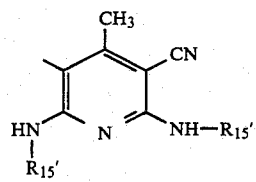 (f₁)
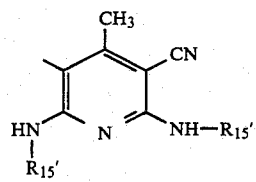 (g₁)
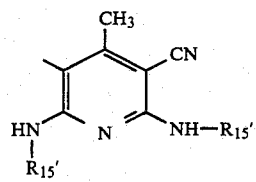 (h₁)
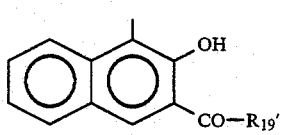 (i₁)
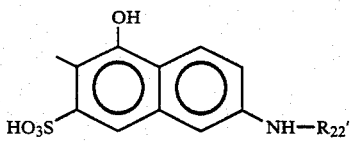
(k₁)
in which
R₂′ is a group of the formula
—N(R₁″)₂ or N⊕(R₂″)₂R₂b′A⊖,
where
each R₂″ independently is $C_{1-4}$alkyl; and
R₂b′ is methyl, ethyl or benzyl;
R₉′ is
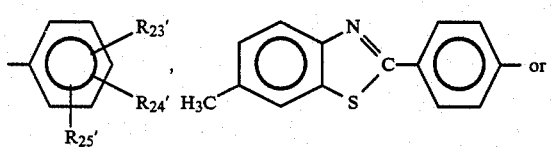
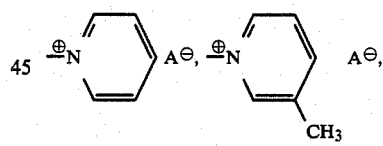
R₁₀′ and R₁₁′ independently of each other are —CH₃, —C₂H₅, —OCH₃ or —OC₂H₅;
R₁₃′ is —CN, —CONH₂,
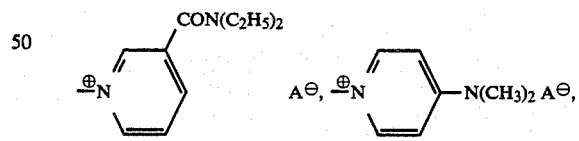
or hydrogen;
R₁₄′ is hydrogen, —CH₃, —C₂H₅,
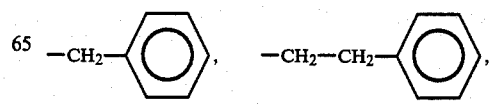

-continued

—NH—⟨phenyl⟩,

—(CH$_2$)$_2$—OH, —(CH$_2$)$_3$OCH$_3$, —(CH$_2$)$_2$—CN,
—(CH$_2$)$_3$—N(CH$_3$)$_2$, —(CH$_2$)$_3$—N$^⊕$(CH$_3$)$_3$A$^⊖$ or

—(CH$_2$)$_3$—N$^⊕$(CH$_3$)$_2$—CH$_2$—⟨phenyl⟩ A$^⊖$;

each R$_{15}'$ independently is —(CH$_2$)$_2$OH, —(CH$_2$)$_3$OCH$_3$, —(CH$_2$)$_3$N(CH$_3$)$_2$ or —(CH$_2$)$_3$N(C$_2$H$_5$)$_2$,
R$_{18}'$ is —C(=N$^⊕$H)NH$_2$ A$^⊖$, ⟨phenyl⟩ or —⟨phenyl⟩—NHCOCH$_2$N$^⊕$(CH$_3$)$_3$A$^⊖$;

R$_{19}'$ is —NH—(CH$_2$)$_3$—N(R$_1''$)$_2$— or

—NH—⟨phenyl⟩—NO$_2$,

R$_{20}'$ is —CH$_3$, C$_2$H$_5$ or

—CH$_2$—⟨phenyl⟩;

R$_{21}'$ is —CH$_3$, —C$_2$H$_5$, —(CH$_2$)$_2$—N$^⊕$(CH$_3$)$_3$A$^⊖$ or

—(CH$_2$)$_2$—N$^⊕$⟨pyridyl⟩ A$^⊖$,

R$_{22}'$ is

⟨triazine with R$_{31}'$ substituents⟩, each R$_{23}'$, R$_{24}'$ and R$_{25}'$ independently of one another is hydrogen, chlorine, methyl, ethyl, methoxy or ethoxy;
R$_{31}'$ is —NH—(CH$_2$)$_m$—N(CH$_3$)$_2$ or —NH—(CH$_2$)$_m$N(C$_2$H$_5$)$_2$;
K$_a'$ is a coupling component of formula (a$_1$), (b$_1$), (c$_1$), (e$_1$), (f$_1$), (g$_1$), (h$_1$), (i$_1$) or (k$_1$) defined under symbol K'.

Preferred compounds of formula III are of formula IV $$(R_1'')_2N-(CH_2)_n-NH-CO-\text{[pyridone ring with NH}_2\text{, NH}_2\text{, O, }(CH_2)_n-N(R_1'')_2\text{]}-N=N-\text{[phenyl-R}_3'\text{]}-X''-\text{[phenyl-R}_3'\text{]}-N=N-K''$$
(IV)

in which
R$_3'$ is hydrogen, chloro, methyl or methoxy;
X'', when both R$_3'$ s are hydrogen, is
X$_1$, X$_{10}$, X$_{12}$, X$_{17}$, X$_{27}$, X$_{51}$, X$_{52}$, X$_{54}$, X$_{64}$, X$_2'$, X$_2''$, X$_{14}'$, X$_{19}'$, X$_{20}'$, X$_{19}''$, X$_{19}'''$, X$_{20}''$, X$_{21}'$, X$_{32}'$, X$_{32}''$, X$_{34}'$, X$_{34}''$, X$_{34}'''$, X$_{34}^{iv}$, X$_{34}^{v}$ or X$_{34}^{vi}$;
and X'', when one R$_3'$ is chloro, methyl or methoxy, is a direct bond;
K'' is a group of formula (a$_1$), (b$_1$), (d$_1$), (e$_1$), (f$_1$), (g$_1$), (h$_1$), (i$_1$), (k$_1$) or (c$_2$)

$$-\underset{CH_3}{\overset{C-OH}{C}}-CONH-\text{[phenyl]}-X'-\text{[phenyl]}-NHCO-\underset{CH_3}{\overset{C-OH}{C}}-N=N-\left[\text{[phenyl]}-C\overset{S}{\underset{N}{\diagup}}\text{[benzothiazole-CH}_3\text{]}\right]-(CH_2-R_a')_{p'}$$

where p' is a number from 1 to 2, preferably on average 1.5.

Compounds of formula I where Z is hydrogen may be prepared by cyclising 2 moles of a compound of formula V $$NC-CH_2-\overset{O}{\underset{\|}{C}}-NH-T-R$$     V where the symbols are defined above, in the presence of a substantially water-free organic medium (for example an alcohol) at high temperatures in the presence of a base (for example an alcoholate). The compounds of formula V are known or can be formed by known methods from known compounds.

Compounds of formula I where Z is other than hydrogen can be formed by reacting a diazotised amine of formula VI

D—NH$_2$   VI with a compound of formula I where Z is hydrogen.

Compounds of formula I, where Z is

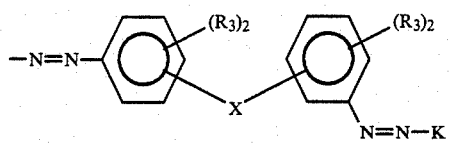

can be prepared by reacting 1 mole of a tetrazotised diamine of formula VII

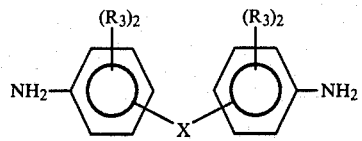

with 2 moles of a compound of formula I where Z is hydrogen, or with 1 mole of a compound of formula I where Z is hydrogen and 1 mole of a compound of formula VIII

H—K   VIII where K is as defined above other than of formula (a). Compounds of formulae VI, VII and VIII are known or may be prepared by known methods from known compounds.

Coupling can be carried out by known methods for example in aqueous medium at temperatures from $-10°$ C. to room temperature optionally in the presence of a coupling accelerator for example urea or pyridine.

Further, according to the invention there are provided polymers containing at least two recurring units of one of formulae X to XIII

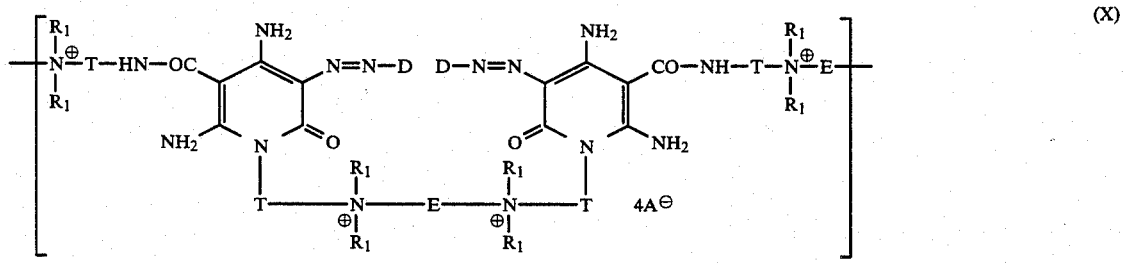

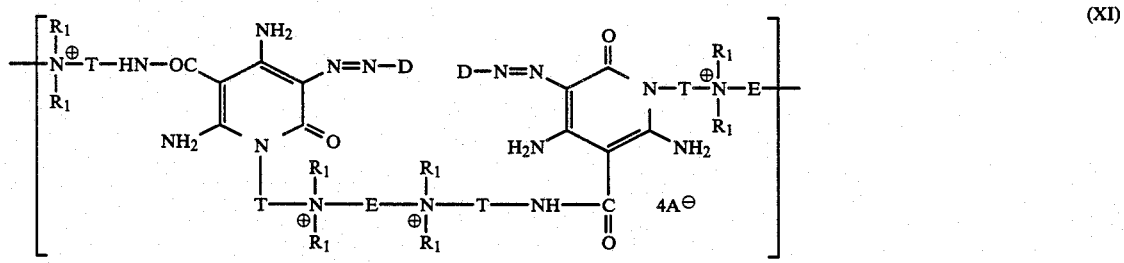

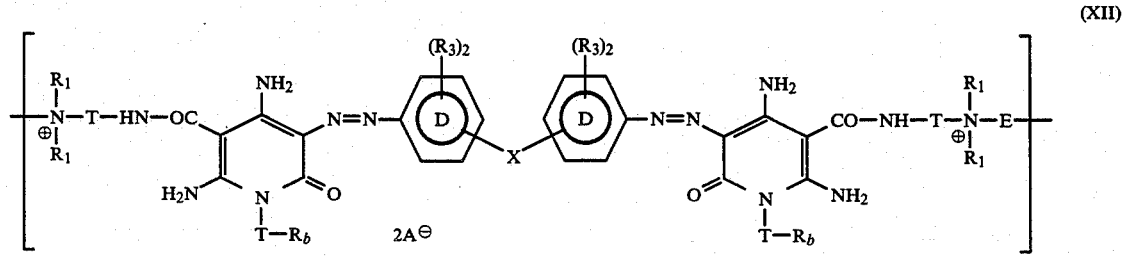

(XIII)
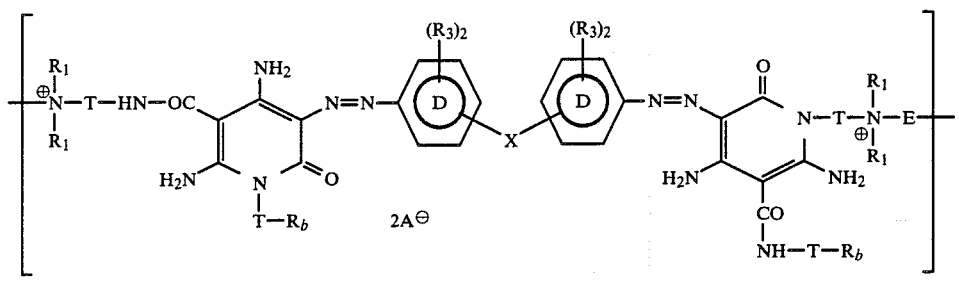
in which E is a bridging group $E_1$ to $E_{70}$
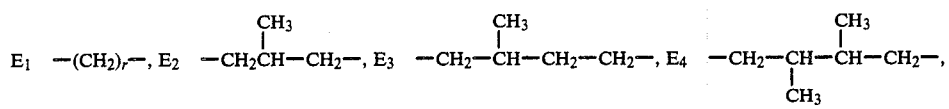
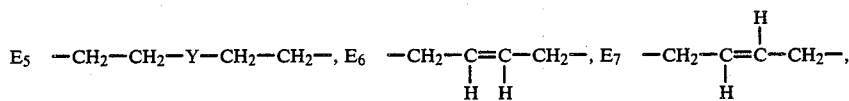
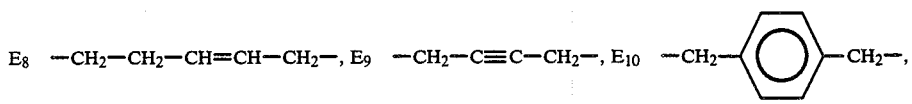
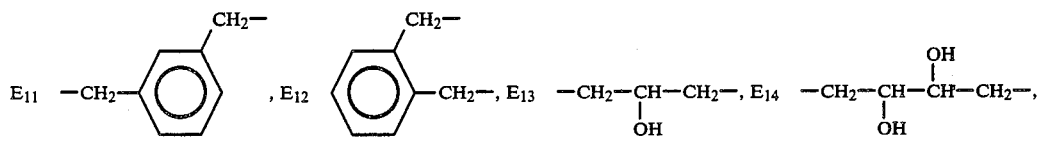
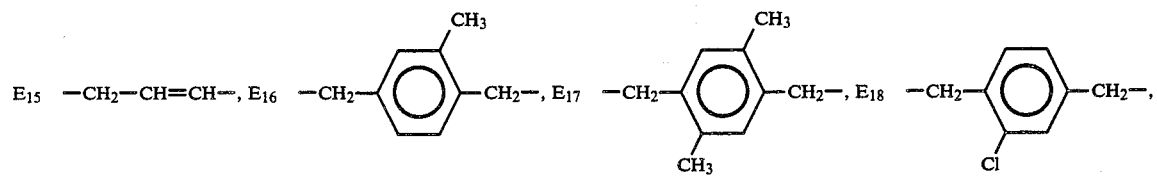
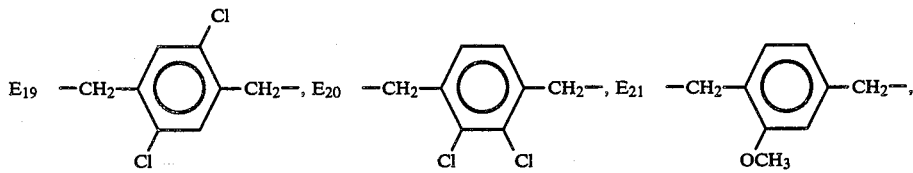
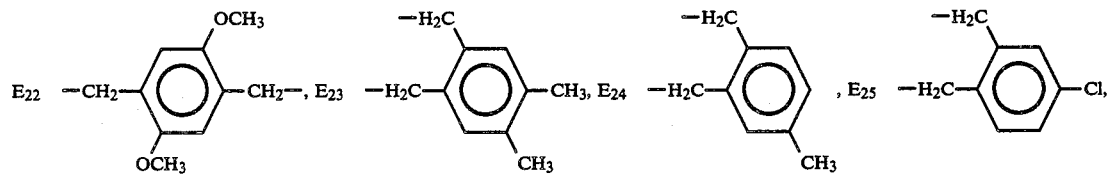
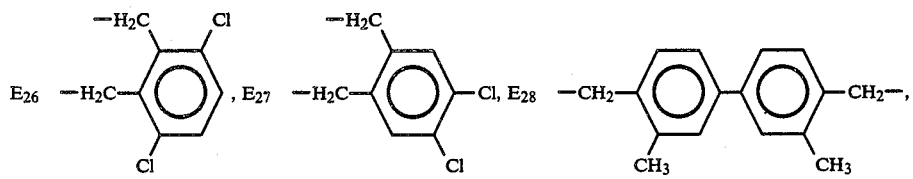

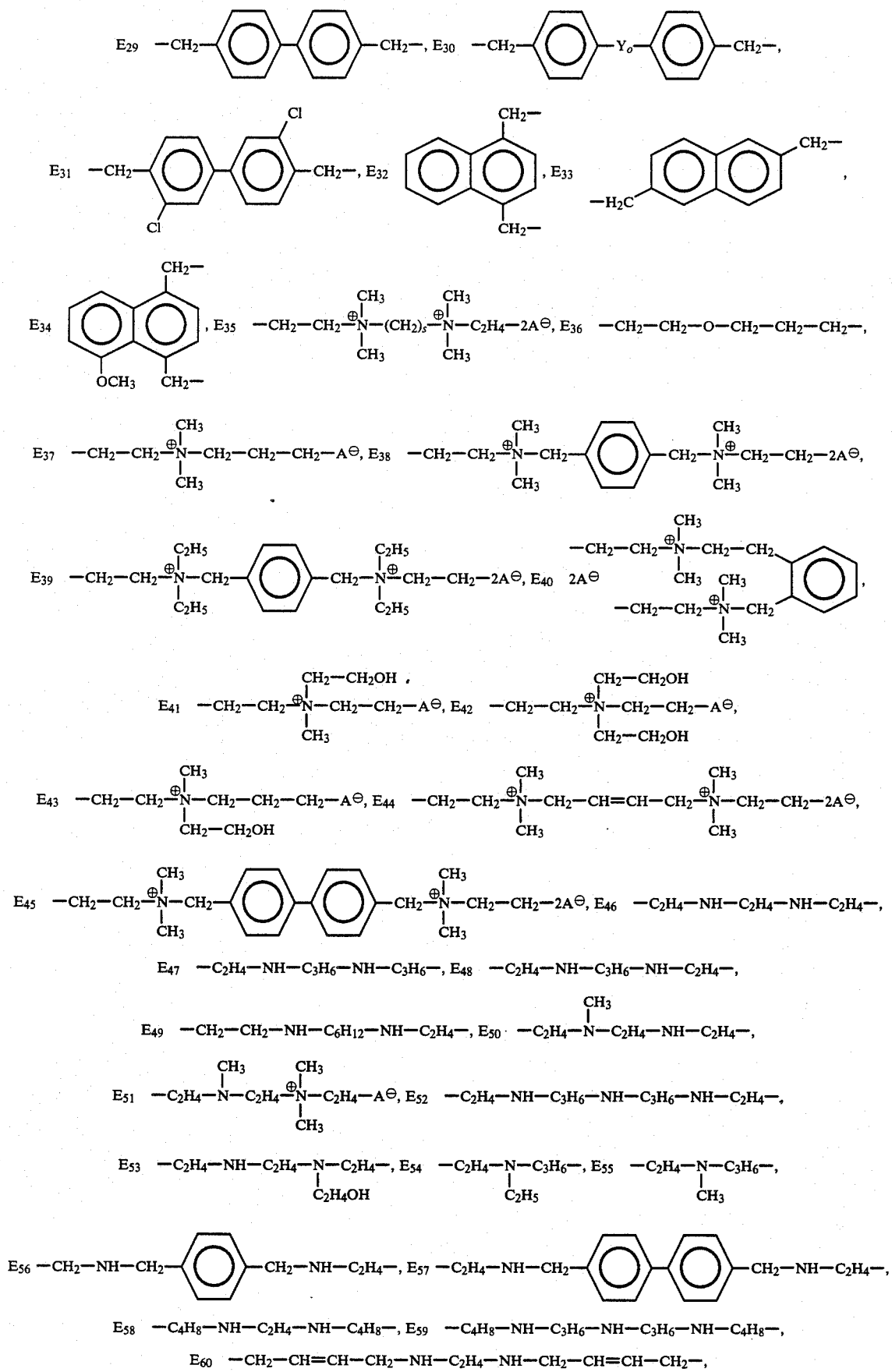

-continued

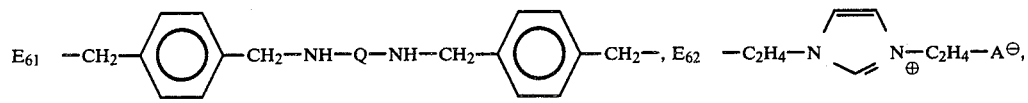

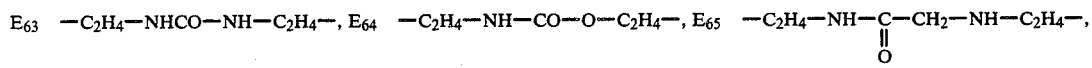

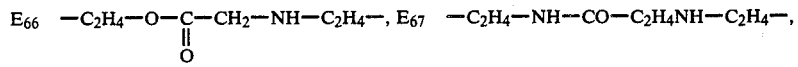

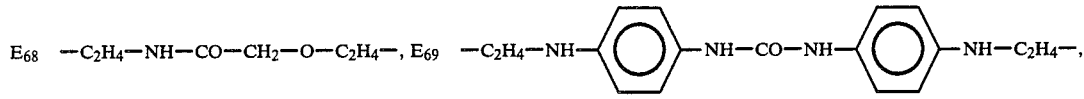

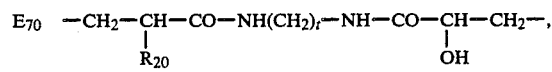

r is an integer from 2 to 6 inclusive;
t is an integer 1 to 6 inclusive;

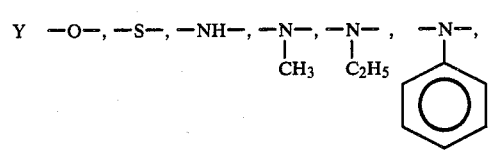

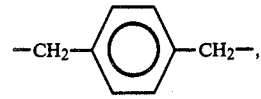

$Y_o$ is —$(CH_2)_q$—, —O—, —S—, —CO—, —COO—, —$SO_2$—, —$SO_2$—O—, —O—$SO_2$—O—, —CO—NH—, —NH—CO—NH—, —NH—C-S—NH—, —NH— or

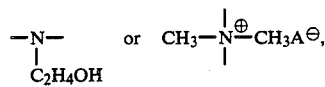

s is an integer from 2 to 10 inclusive;

Q is —$C_2H_4$—, —$C_3H_6$—, —$C_6H_{12}$ or

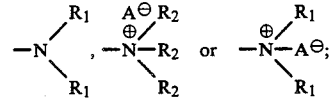

$R_b$ is in which case one bond is attached to T and the remaining bond is attached to E of another unit of formula XII or XIII respectively; and the other symbols are as defined earlier in the specification.

Preferably 2 to 25, more preferably 2 to 10 and most preferably 3 to 6 of one of the recurring units of formulae $X_a$ to XIII are present in a polymer according to the invention.

Preferred polymers according to the invention are those of formulae X to XIII$_a$

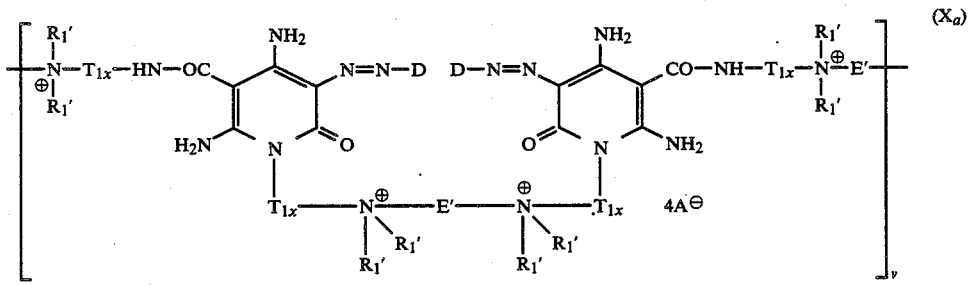

or of formula

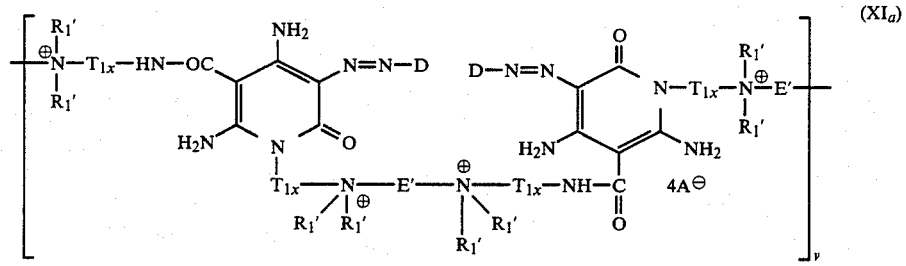

(XIa)

or of formula

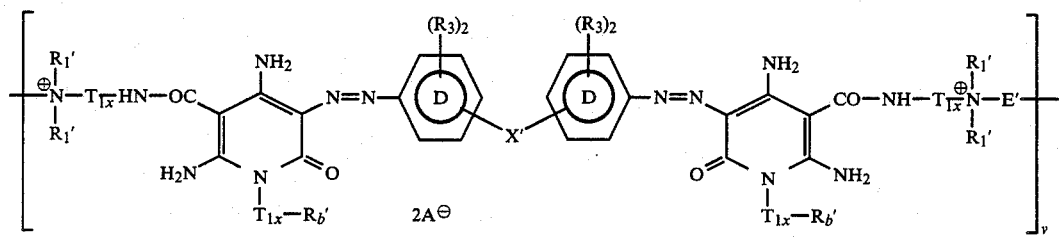

(XIIa)

or of formula

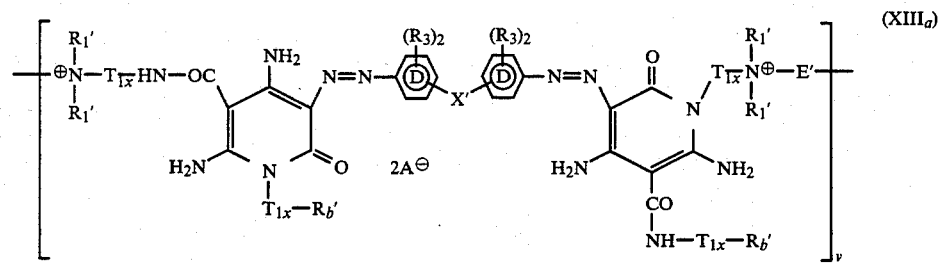

(XIIIa)

in which $T_{1x}$ is $-(CH_2)_n-$;

X' is as defined above;

E' is $E_2$, $E_3$, $E_4$, $E_6$, $E_7$, $E_{10}$, $E_{11}$, $E_{12}$, $E_{13}$, $E_{14}$, $E_{16}$, $E_{17}$, $E_{18}$, $E_{21}$, $E_{22}$, $E_{28}$, $E_{29}$, $E_{31}$, $E_{32}$, $E_{35}$, $E_{38}$, $E_{41}$, $E_{46}$, $E_{63}$ or $E_{71}$ $-(CH_2)_2-$, $E_{72}$ $-(CH_2)_3-$,

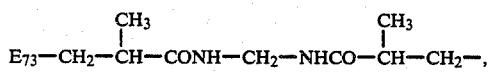

$E_{74}$ $-(CH_2)_4-$, $E_{75}$ $-(CH_2)_5-$, $E_{76}$ $-(CH_2)_6-$, $E_{77}$ $-CH_2CH_2-O-CH_2CH_2-$,

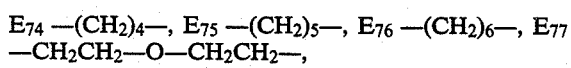

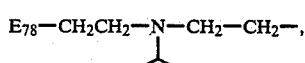

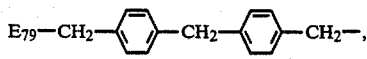

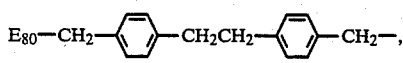

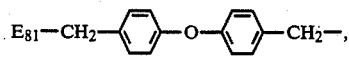

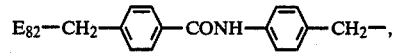

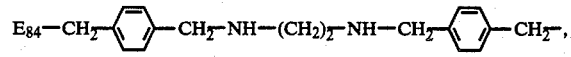

$E_{85}$ $-CH_2-CH_2-CO-NH-(CH_2)_2-NH-CO-CH_2-CH_2-$ $R_b'$ is $-N(R_1')_2$, $-N^{\oplus}(R_2')_3 A^{\ominus}$ or

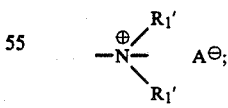

where the remaining bond is attached to E' of another unit of formula XIIa or XIIIa respectively;

v is a number from 2 to 25;

and the other symbols are as defined earlier in the specification.

Preferably in polymers of the invention containing recurring units of formulae $X_a$ to $XIII_a$, $R_1'$ is preferably $R_1''$;

$R_b'$ is preferably $R_b''$; where $R_b''$ is $-N(R_1'')_2$ or $-N^{\oplus}(R_2'')_3 A^{\ominus}$ or

where one bond is attached to $T_{1x}$ and the remaining free-bond is attached to E of another recurring unit;

E' is preferably E'' where E'' is $E_2, E_3, E_4, E_6, E_7, E_{10}, E_{11}, E_{12}, E_{13}, E_{14}, E_{16}, E_{21}, E_{28}, E_{29}, E_{31}, E_{72}, E_{74}, E_{76}, E_{77}, E_{78}, E_{79}, E_{80}, E_{81}$ or $E_{85}$; and X' is preferably X''.

Polymers containing at least 2 recurring units of any one of formulae X to XIII can be prepared by reacting a compound of formula XIV

E—(Hal)$_2$                           (XIV)

where Hal is a halogen atom,
with the appropriate amount of a corresponding mono or polyazo compound of formula I preferably in an organic medium at room temperature or at a raised temperature in the presence of an acid receptor.

In this specification when T has the significance of an alkylene group this is preferably —(CH$_2$)$_n$—, more preferably —(CH$_2$)$_2$—.

When $R_1$ or $R_2$ has the significance of an alkyl group this is preferably ($C_{1-12}$alkyl, more preferably ($C_{1-4}$alkyl, and most preferably methyl or ethyl.

When $R_{14}$ has the significance of a substituted alkyl group this is preferably benzyl or phenylethyl.

Unless indicated to the contrary any alkyl group is preferably $C_{1-4}$alkyl, more preferably methyl or ethyl, any alkoxy group is $C_{1-4}$alkoxy, more preferably ethoxy or methoxy and any halogen present is chlorine or bromine, more preferably the former.

In the compounds of formula I or formula II (where appropriate) and recurring units of formulae X to XIII the preferences for each symbol are given below:

T is preferably $T_1$, more preferably —(CH$_2$)$_n$—;
R is preferably R', more preferably R'', most preferably —N($R_1''$)$_2$;
$R_1$ is preferably $R_1'$ more preferably $R_1''$;
$R_2$ is preferably $R_2'$ more preferably $R_2''$;
$R_4$ is preferably $R_4'$;
$R_7$ is preferably $R_7'$;
$R_9$ is preferably $R_9'$;
$R_{10}$ and $R_{11}$ are preferably $R_{10}'$ and $R_{11}'$;
$R_{13}$ is preferably $R_{13}'$;
$R_{14}$ is preferably $R_{14}'$;
$R_{15}$ is preferably $R_{15}'$;
$R_{18}$ is preferably $R_{18}'$;
$R_{19}$ is preferably $R_{19}'$;
$R_{20}$ is preferably $R_{20}'$;
$R_{21}$ is preferably $R_{21}'$;
$R_{22}$ is preferably $R_{22}'$;
$R_{23}, R_{24}$ and $R_{25}$ are preferably $R_{23}', R_{24}'$ and $R_{25}'$;
X is preferably X', more preferably X'';
K is preferably K', more preferably K'';
p is preferably p';
$K_a$ is preferably $K_a'$;
E is preferably E' more preferably E''.

All the symbols given above are defined earlier in the specification.

In the compounds or polymers according to the invention the anion $A^\ominus$ may be exchanged for other anions, e.g. with the aid of an ion exchanger, or by means of a reaction with salts or acids, optionally in several stages, e.g. by forming the hydroxide or the bicarbonate, or in accordance with German Published Specification No. 2,001,748 or 2,001,816.

The anion $A^\ominus$ is non-chromophoric and may be one which is conventional in basic dyestuff chemistry. The anion $A^\ominus$ is understood to include both organic and inorganic ions, e.g. halide, such as chloride or bromide, sulphate, bisulphate, methyl sulphate, aminosulphonate, perchlorate, benzenesulphonate, oxalate, maleinate, acetate, propionate, lactate, succinate, tartrate, malate, methanesulphonate or benzoate ions, or complex anions, such as those of zinc chloride double salts, and furthermore the anions of the following acids: boric acid, citric acid, glycolic acid, diglycolic acid or adipic acid, or addition products of orthoboric acid with polyalcohols, e.g. cis-polyols.

The new compounds or polymers according to the invention may be used as dyestuffs or they may be used in the form of aqueous, e.g. concentrated stable solutions or as granules in quaternised form and/or in the form of the corresponding salts of mineral acids or organic acids, for dyeing all types of fibre material, cellulose, cotton or leather, but especially paper or paper products, and also for bast fibres, such as hemp, flax, sisal, jute, coir or straw.

The dyestuffs may also be employed in the production of bulk-dyed, sized and unsized paper. They may be similarly employed for dyeing paper by dipping. Paper, leather and cellulose can be dyed in accordance with known methods.

In paper production, the dyestuffs according to the invention and their preparations do not colour the back water at all, or only slightly which is particularly advantageous for purification of the back water. The dyestuffs according to the invention are highly substantive, do not mottle when dyed on paper, and are substantially insensitive to pH. The dyeings on paper are notable for their good light fastness properties. After long-term exposure to light, the shade alters tone-in-tone. The dyed papers are wet-fast, not only to water, but also to milk, soap water, sodium chloride solutions, fruit juices and sweetened mineral water, and because of their good alcohol fastness, they are also resistant to alcoholic beverages; furthermore, when dyed on paper, they have a very stable shade.

The dyestuffs according to the invention may be used for dyeing, padding or printing polyacrylonitrile textiles, or polyamide or polyester textiles which are modified by anionic groups.

In the following Examples all parts and percentages are by weight and all temperatures are given in degrees Centigrade.

EXAMPLE 1

(a) Preparation of the coupling component of formula

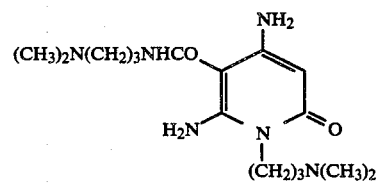

11.3 g of ethyl cyanoacetate are added dropwise whilst cooling to a solution of 10.2 g of dimethylaminopropylamine in 200 ml of absolute ethanol, so that the temperature of the reaction solution remains constantly below 35°. The solution is stirred at 30°–35° until thin-layer chromatography indicates that formation of cyanoacetic acid dimethylaminopropylamide has ceased. Then, 1.7 g of sodium ethylate are added to the solution, which is boiled under reflux for 14 hours. The solvent is then removed under vacuum on a rotary evaporator and the remaining brown oil is taken up in 200 ml of dilute hydrochloric acid. The solution thus obtained can be used as such for dyestuff syntheses.

In the following Table I the composition of further coupling components is given. They may be produced analogously to the method described in Example 1 from suitable starting products and are of formula (Ia) for $K_{12}$ and $K_{13}$ or (Ib) for $K_1$ to $K_{11}$ and $K_{14}$ and $K_{15}$

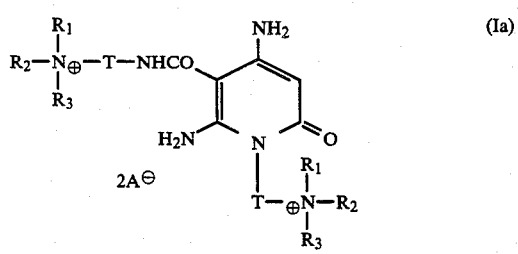

or

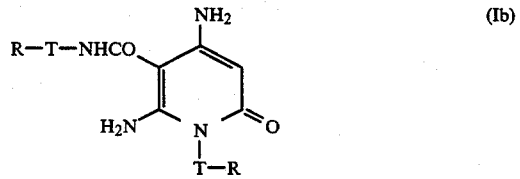

where in formula $I_b$, R is

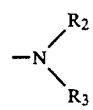

for $K_1$ to $K_{11}$ and R is —OH for $K_{14}$ to $K_{15}$:

TABLE I

| Coupling Component K | $R_1$ | $R_2$ | $R_3$ | T |
|---|---|---|---|---|
| K1 | — | —CH$_3$ | —CH$_3$ | —(CH$_2$)$_2$— |
| K2 | — | —C$_2$H$_5$ | —C$_2$H$_5$ | " |
| K3 | — | —CH(CH$_3$)$_2$ | —CH(CH$_3$)$_2$ | " |
| K4 | — | —C$_4$H$_9$ | —C$_4$H$_9$ | " |
| K5 | — | —H | —CH$_3$ | (CH$_2$)$_3$— |
| K6 | — | —CH$_3$ | " | " |
| K7 | — | —C$_2$H$_5$ | —C$_2$H$_5$ | " |
| K8 | — | " | " | —(CH$_2$)$_4$— |
| K9 | — | " | " | —(CH$_2$)$_3$CH—<br>　　　　　CH$_3$ |
| K10 | — | —H | —H | —(CH$_2$)$_3$— |
| K11 | — | —H | —H | —(CH$_2$)$_2$— |
| K12 | CH$_3$— | —CH$_3$ | —CH$_3$ | —(CH$_2$)$_3$— |
| K13 | C$_6$H$_5$CH$_2$— | " | " | " |
| K14 | — | — | — | —(CH$_2$)$_2$— |
| K15 | — | — | — | —(CH$_2$)$_3$— |

EXAMPLE 1(b)

13.8 g of o-nitroaniline are suspended in 200 ml of water, whilst adding 50 ml of 10N hydrochloric acid. 20 ml of a 5N sodium nitrite solution are added dropwise at 0°–5°, over the course of ca. 45 minutes, to the brown suspension. After the addition of the nitrite, unspent nitrous acid is decomposed with aminosulphonic acid. The diazonium salt solution is filtered by adding decolourising carbon, to produce a clear yellow solution. This solution is then added dropwise over 30 minutes at room temperature to a copper solution containing hydrochloric acid and containing 34.5 g of 4,6-diamino-1-(dimethylaminopropyl)-5-(3'-dimethylaminopropyl)-carbamoyl-1,2-dihydropyridin-2-one. During this addition, the pH is kept at between 2 and 3 by adding simultaneously a solution of caustic soda. When coupling has ended, the reaction mixture is rendered alkaline with ammonia solution, the dyestuff suspension is heated for a short time to 60° and allowed to cool to room temperature. After filtration, a dyestuff of the following formula

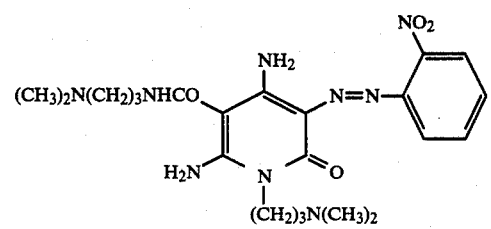

is obtained.

From slightly acidic solutions, this dyestuff dyes polyacrylonitrile, cotton, leather and paper in yellow shades. Because of its good solubility, the dyestuff is especially suitable for the gel-dyeing of polyacrylonitrile.

In Table II further dyestuffs of the formula

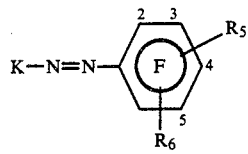

are given. They may be produced by an analogous method to that described in Example 1b from suitable starting products.

TABLE II

| EX. No. | Radical K of Coupling Component No. of Tab. I | Definition and Position of $R_5$ in ring F | Definition and Position of $R_6$ in ring F |
|---|---|---|---|
| 2 | K6 | —H | —H |
| 3 | K6 | 3-Cl | —H |
| 4 | K6 | 4-Cl | —H |
| 5 | K6 | 2-Cl | 5-Cl |
| 6 | K6 | 2-$NO_2$ | —H |
| 7 | K6 | 4-$NO_2$ | —H |
| 8 | K6 | 2-$NO_2$ | 4-Cl |
| 9 | K6 | 2-Cl | 4-$NO_2$ |
| 10 | K6 | 4-N=N—⟨⟩ | —H |
| 11 | K6 | 4-O—⟨⟩—Cl | —H |
| 12 | K6 | 4-$OCH_3$ | —H |
| 13 | K1 | 4-$NO_2$ | —H |
| 14 | K2 | 2-Cl | 5-Cl |
| 15 | K3 | —H | —H |
| 16 | K4 | —H | —H |
| 17 | K5 | 2-$NO_2$ | —H |
| 18 | K7 | 2-$NO_2$ | —H |
| 19 | K8 | —H | —H |
| 20 | K9 | —H | —H |
| 21 | K10 | —H | —H |
| 22 | K11 | —H | —H |
| 23 | K12 | 4-N=N—⟨⟩ | —H |
| 24 | K13 | 4-O—⟨⟩—Cl | —H |
| 25 | K6 | 4-N=N—⟨⟩-$CH_3$ | 3-$CH_3$ |
| 25a | K14 | 2-$NO_2$ | —H |

EXAMPLE 26

22.7 g of 4,4'-diaminobenzanilide are dissolved in 200 ml of water at 90° with 50 ml of 10N hydrochloric acid. 50 ml of 4N sodium nitrite solutions are added to the suspension which is obtained upon cooling to 0°–5°. After the addition of the nitrite, the unspent nitrous acid is broken down with aminosulphonic acid. The diazonium salt solution is filtered by adding decolourising carbon. The clear solution is added in drops in 30 minutes to a copper solution containing hydrochloric acid, and containing 69 g of 4,6-diamino-1-(dimethylaminopropyl)-5-(N-dimethylaminopropylcarbamoyl)-1,2-dihydropyridin-2-one. During coupling, the pH value is kept at between 2 and 3 by adding simultaneously a solution of caustic soda. When coupling has ended, the reaction mixture is rendered alkaline with ammonia solution, the dyestuff suspension is heated for a short time to 60° and allowed to cool to room temperature. After filtration, a dyestuff of the formula

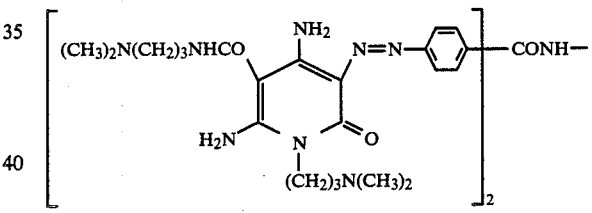

is obtained. From slightly acidic solutions, it dyes polyacrylonitrile, cotton, leather and paper in reddish-yellow shades.

Table III gives the composition of further dyestuffs of the formula

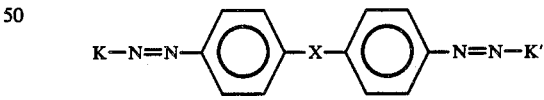

and these dyestuffs may be made by a method analogous to that of Example 26.

TABLE III

| EX. No. | Radical K of Coupling Component No. of Table I | Radical K' of Coupling Component No. of Table I | Definition of X from the description |
|---|---|---|---|
| 27 | K6 | K6 | $X_{51}$ |
| 28 | K6 | K6 | $X_2'$ |
| 29 | K6 | K6 | $X_2''$ |
| 30 | K6 | K6 | $X'_{34}$ |
| 31 | K6 | K6 | $X''_{34}$ |
| 32 | K6 | K6 | $X_{67}$ ($R_6$ = $(CH_2)_2$—) |

TABLE III-continued

| EX. No. | Radical K of Coupling Component No. of Table I | Radical K' of Coupling Component No. of Table I | X |
|---|---|---|---|
| 33 | K6 | K6 | $X_{68}$ ($R_7 = $ 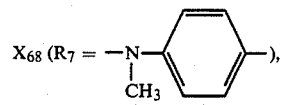), $R_6 = -(CH_2)_2-$ |
| 34 | K6 | K6 | $X_{72}$ |
| 35 | K1 | K1 | $X_{11}$ |
| 36 | K2 | K2 | $X_2'$ |
| 37 | K1 | K1 | $X_2''$ |
| 38 | K1 | K1 | $X_{34}'$ |
| 39 | K3 | K3 | $X_{67}$ (as Example 32) |
| 40 | K1 | K1 | $X_{67}$ (as Example 33) |
| 41 | K1 | K1 | $X_{72}$ |
| 42 | K4 | K4 | $X_{11}$ |
| 43 | K4 | K4 | $X_2'$ |
| 44 | K4 | K4 | $X_2''$ |
| 45 | K4 | K4 | $X_{34}'$ |
| 46 | K5 | K5 | $X_{11}$ |
| 47 | K5 | K5 | $X_2'$ |
| 48 | K5 | K5 | $X_2''$ |
| 49 | K5 | K5 | $X_{34}'$ |
| 50 | K7 | K7 | $X_{11}$ |
| 51 | K7 | K7 | $X_2'$ |
| 52 | K7 | K7 | $X_2''$ |
| 53 | K7 | K7 | $X_{34}'$ |
| 54 | K8 | K8 | $X_2''$ |
| 55 | K8 | K8 | $X_{34}'$ |
| 56 | K9 | K9 | $X_{34}'$ |
| 57 | K9 | K9 | $X_{67}$ (as Example 32) |
| 58 | K10 | K10 | $X_{34}'$ |
| 59 | K10 | K10 | $X_{11}$ |
| 60 | K11 | K11 | $X_{34}'$ |
| 61 | K11 | K11 | $X_{34}''$ |
| 62 | K12 | K12 | $X_{34}'$ |
| 63 | K13 | K13 | $X_{34}'$ |
| 64 | K6 | K1 | $X_{34}'$ |
| 65 | K6 | K7 | $X_{34}'$ |
| 66 | K6 | K4 | $X_{34}'$ |
| 67 | K6 | K4 | $X_{11}$ |
| 68 | K6 | K7 | $X_{11}$ |
| 69 | K6 | K1 | $X_{11}$ |
| 69a | K14 | K14 | $X_{11}$ |

| EX. No. | Radical K of Coupling Component No. of Table I | Radical K' of Coupling Component No. of Table I | X |
|---|---|---|---|
| 70 | K12 | 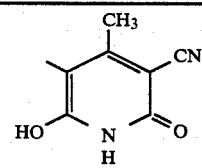 | $X_{34}'$ |
| 71 | K6 | " | $X_{11}$ |
| 72 | K6 | 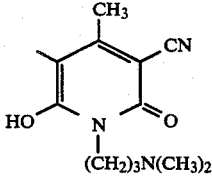 | $X_{11}$ |
| 73 | K6 | " | $X_{34}'$ |
| 74 | K6 | 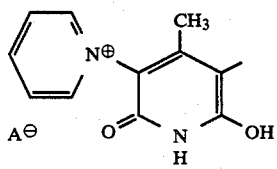 | $X_{34}'$ |
| 74a | K14 | " | $X_{11}$ |
| 75 | K6 | " | $X_{11}$ |

TABLE III-continued

| | | Structure | |
|---|---|---|---|
| 76 | K6 | (CH₃)₂N-pyridine-N⁺-pyridone with CH₃, CH₃, OH substituents; A⁻ | $X'_{34}$ |
| 77 | K6 | " | |
| 78 | K6 | 2,6-bis[(CH₃)₂N(CH₂)₃NH]-3,4-dimethylpyridine | $X_{11}$ |
| 79 | K6 | 3-methyl-1-phenyl-5-hydroxypyrazole | $X_{11}$ |
| 80 | K6 | CH₃COCH(—)CONH—(2-methoxyphenyl) | $X_{11}$ |
| 81 | K6 | 4-CH₃-C₆H₄-N(C₂H₅)(CH₂)₂N⁺(CH₃)₃ A⁻ | $X'_{34}$ |
| 82 | K12 | 1-methyl-3-hydroxy-2-naphthoyl-NH(CH₂)₃N(CH₃)₂ | $X_{11}$ |
| 83 | K6 | 4-hydroxy-3-methyl-naphthalene-2-sulfonic acid, 7-(NHCOCH₂-pyridinium) A⁻ | $X_{11}$ |
| 84 | K6 | CH₃COCH(CONH—)—phenyl—benzothiazole with CH₃ | $X_{34}$ |

EXAMPLE 85

14 g of the dyestuff of Example 26 are stirred into 100 ml of 2-ethoxyethanol, and then 10 ml of 10% caustic soda are added. 2.2 g of α,α-dichloro-p-xylene are then added in small portions at room temperature, over the course of 3 hours, and the mixture is stirred for a further 15 hours at room temperature and for one hour at 35°. The separated dyestuff is filtered off. The resulting polymer contains 3–6 recurring units of the formula

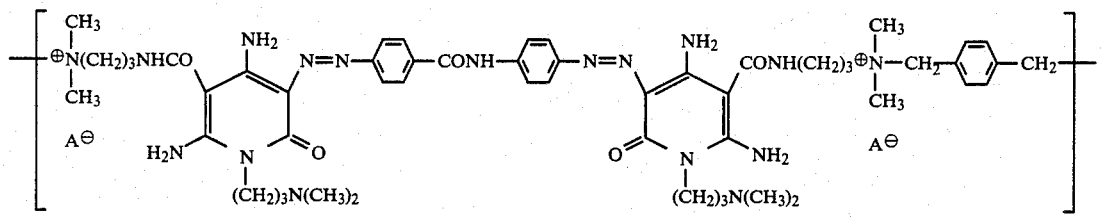

The polymeric dye dyes paper reddish-yellow shades. The dyeings are notable for their particularly good wet fastness properties.

In Table IV polymers containing 3-6 recurring units of formula

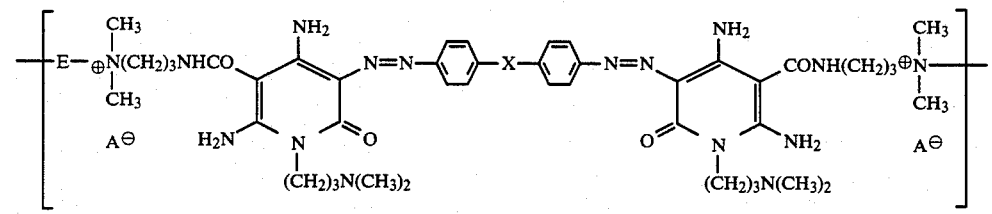

are shown which can be prepared by a method analogous to that of Example 85.

TABLE IV

| EXAMPLE No. | X | Definition of E |
|---|---|---|
| 86 | $X_{51}$ | $E_{10}$ |
| 87 | $X_2'$ | $E_{10}$ |
| 88 | $X_2''$ | $E_{10}$ |
| 89 | $X_{34}'$ | $E_{10}$ |
| 90 | $X_{34}'$ | $E_{13}$ |
| 91 | $X_{34}'$ | $E_{74}$ |
| 92 | $X_{34}'$ | $E_{11}$ |

EXAMPLES 93 TO 96

In Table V polymers containing recurring units of the formula

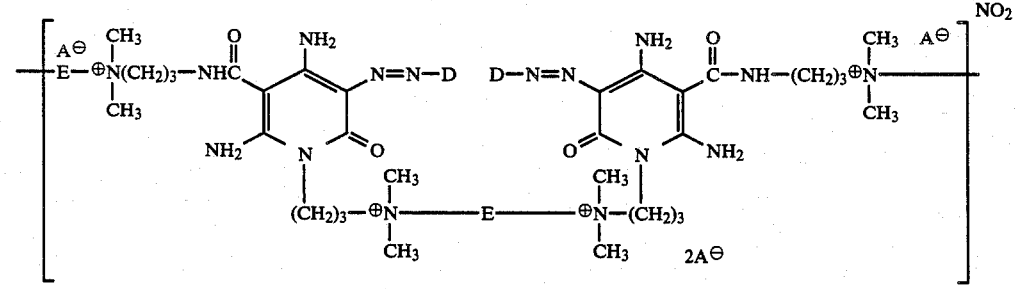

can be prepared by a method analogous to that of Example 85.

TABLE V

| EX. No. | Definition of E | D |
|---|---|---|
| 93 | $E_{10}$ | |
| 94 | $E_{13}$ | |
| 95 | $E_{74}$ | |
| 96 | $E_{11}$ | |

EXAMPLES 97 TO 100

In Table VI polymers containing 3 to 6 recurring units of the formula

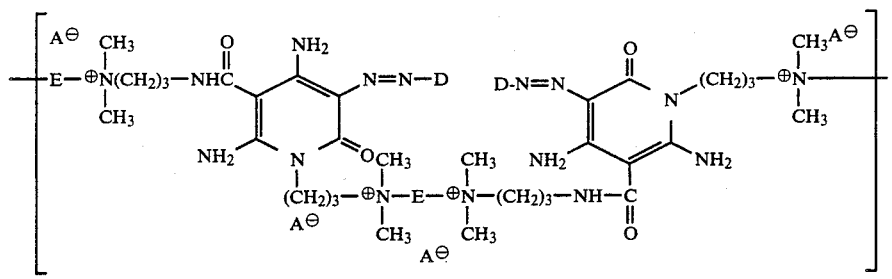

may be prepared by a method analogous to that of Example 85.

TABLE VI

| EX. No. | Definition of E | D |
|---|---|---|
| 97 | $E_{10}$ | (2-nitrotoluene structure) |
| 98 | $E_{13}$ | (azobenzene structure) |
| 99 | $E_{74}$ | (4-chlorotoluene structure) |
| 100 | $E_{11}$ | (2-nitrotoluene structure) |

EXAMPLES 101 TO 107

In Table VII polymers containing 3 to 6 recurring units of the formula

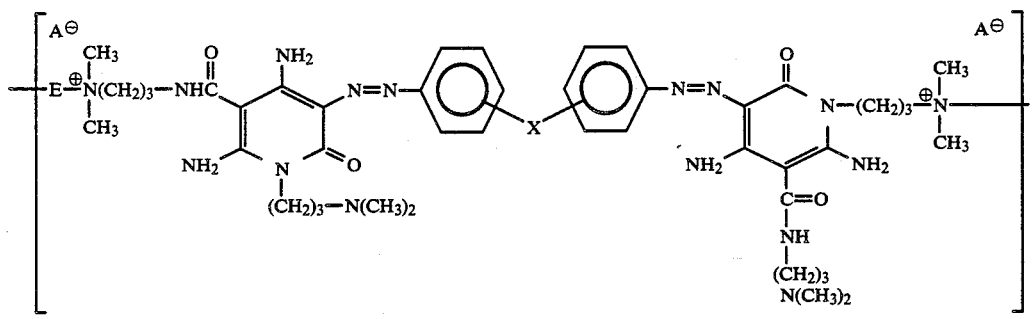

may be prepared by a method analogous to that of Examples 85, from suitable starting materials.

TABLE VII

| Example No. | X | Definition of E |
|---|---|---|
| 101 | $X_{51}$ | $E_{10}$ |
| 102 | $X_2'$ | $E_{10}$ |
| 102 | $X_2''$ | $E_{10}$ |
| 104 | $X_{34}'$ | $E_{10}$ |
| 105 | $X_{34}'$ | $E_{13}$ |
| 106 | $X_{34}'$ | $E_{74}$ |
| 107 | $X_{34}'$ | $E_{11}$ |

Dyeings on paper made from dyestuffs of Examples 2 to 26 and 28 to 30 are greenish-yellow to orange, from those of Examples 27 and 31 to 84 and from those of Examples 85 to 107 are yellow to yellowish-green.

The significances of X and E in the above Tables are as defined earlier in the specification.

DYEING EXAMPLE A

70 Parts of chemically bleached sulphite cellulose (of pinewood) and 30 parts of chemically bleached sulphite cellulose (of birchwood) are ground in a Hollander in 2000 parts of water. 0.2 Parts of the dyestuff described in Example 26 are sprinkled into this pulp. After mixing for 20 minutes, paper is produced from this pulp. The absorbent paper obtained in this way is dyed reddish-yellow. The waste water is practically colourless.

DYEING EXAMPLE B 0.5 Parts of the dyestuff of Example 26 are dissolved in 100 parts of hot water and cooled to room temperature. This solution is added to 10 parts of chemically bleached sulphite cellulose which have been ground in a Hollander with 2000 parts of water. After thorough mixing for 15 minutes, sizing takes place.

Paper which is produced from this matter has a reddish-yellow shade of average intensity, with good wet fastness properties.

DYEING EXAMPLE C

An absorbent length of unsized paper is drawn through a dyestuff solution of the following composition at 40° to 50°. 0.5 Parts of the dyestuff of Example 26; 0.5 parts of starch and 99.0 parts of water. The excess dyestuff solution is squeezed out through two rollers. The dried length of paper is dyed reddish-yellow with good fastness.

DYEING EXAMPLE D

2 Parts of the dyestuff according to Example 26 are dissolved at 40° in 4000 parts of softened water. 100 Parts of premoistened cotton fabric are entered into the bath, which is heated for 30 minutes to boiling temperature. The bath is kept at boiling temperature for 1 hour, and the water which evaporates is replaced from time to time. The dyeing is then removed from the liquor, rinsed with water and dried. The dyestuff is absorbed practically quantitatively on the fibres; the dye bath is practically colourless. A reddish-yellow dyeing is obtained with good light fastness and good wet fastness.

In Dyeing Examples A to D an appropriate amount of any one of dyestuffs of Examples 1 to 25 and 27 to 107 in liquid or granulate preparation form may be used instead of the amount of the dyestuff of Example 26 to produce good dyeings with good fastness properties.

What is claimed is:

1. A compound of the formula

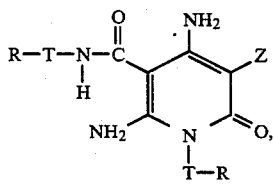

wherein each R is independently $-N(R_1)_2$, $-N^\oplus(R_1)_3 A^\ominus$ or hydroxy, wherein each $R_1$ is independently hydrogen; $C_{1-12}$alkyl; $C_{1-12}$alkyl substituted by halo, cyano, hydroxy, phenyl or carbamoyl; cyclohexyl; cyclohexyl substituted by 1 to 3 $C_{1-4}$alkyl groups; phenyl or phenyl substituted by 1 to 3 $C_{1-4}$alkyl groups or $-N(R_1)_2$ is piperidino, morpholino, piperazino, N'-$C_{1-4}$alkylpiperazino or pyrrolidino, each $R_2$ is independently $C_{1-12}$alkyl; $C_{1-12}$alkyl substituted by halo, cyano, hydroxy, phenyl or carbamoyl; cyclohexyl; cyclohexyl substituted by 1 to 3 $C_{1-4}$alkyl groups; phenyl or phenyl substituted by 1 to 3 $C_{1-4}$alkyl groups or $-N^\oplus(R_2)_3$ is N-$R_2$-piperidinium, N-$R_2$-morpholinium, N-$R_2$-piperazinium, N-$R_2$-N'-$C_{1-4}$alkylpiperazinium, N-$R_2$-pyrrolidinium, pyridinium or pyridinium substituted by 1 to 3 $C_{1-4}$alkyl groups, wherein $R_2$ is as defined above, and $A^\ominus$ is a non-chromophoric anion, each T is independently $C_{1-12}$alkylene or $C_{3-12}$alkenylene, and Z is hydrogen or $-N=N-D$, wherein D is a diazo component radical.

2. A compound according to claim 1 wherein Z is $-N=N-D$.

3. A compound according to claim 1 wherein Z is hydrogen.

4. A compound of the formula

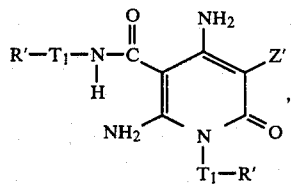

wherein each R' Is independently $-N(R_1')_2$, $-N^\oplus(R_2')_3 A^\ominus$ or hydroxy, wherein each $R_1'$ is independently hydrogen; $C_{1-12}$alkyl; $C_{1-12}$alkyl substituted by halo, cyano, hydroxy, phenyl or carbamoyl; cyclohexyl; cyclohexyl substituted by 1 to 3 $C_{1-4}$alkyl groups; phenyl or phenyl substituted by 1 to 3 $C_{1-4}$alkyl groups or $-N(R_1')_2$ is piperidino, morpholino, piperazino, N'-$C_{1-4}$alkylpiperazino or pyrrolidino, and each $R_2'$ is independently $C_{1-12}$alkyl; $C_{1-12}$alkyl substituted by halo, cyano, hydroxy, phenyl or carbamoyl; cyclohexyl; cyclohexyl substituted by 1 to 3 $C_{1-4}$alkyl groups; phenyl or phenyl substituted by 1 to 3 $C_{1-4}$alkyl groups or $-N^\oplus(R_2')_3$ is N-$R_2'$-piperidinium, N-$R_2'$-morpholinium, N-$R_2'$-piperazinium, N-$R_2'$-N'-$C_{1-4}$alkylpiperazinium, N-$R_2'$-pyrrolidinium, pyridinium or pyridinium substituted by 1 to 3 $C_{1-4}$alkyl groups, each $T_1$ is $C_{1-12}$alkylene or $C_{3-12}$alkenylene, and Z' is hydrogen,

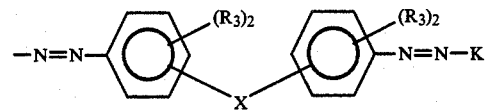

or

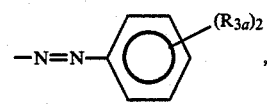

wherein each $R_3$ is independently hydrogen, halo, $C_{1-4}$alkyl or $C_{1-4}$alkoxy, each $R_{3a}$ is independently hydrogen, halo, $C_{1-4}$alkyl, $C_{1-4}$alkoxy, nitro,

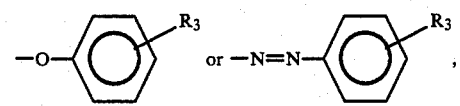

wherein $R_3$ is as defined above, and

K and X are as defined below, wherein K is

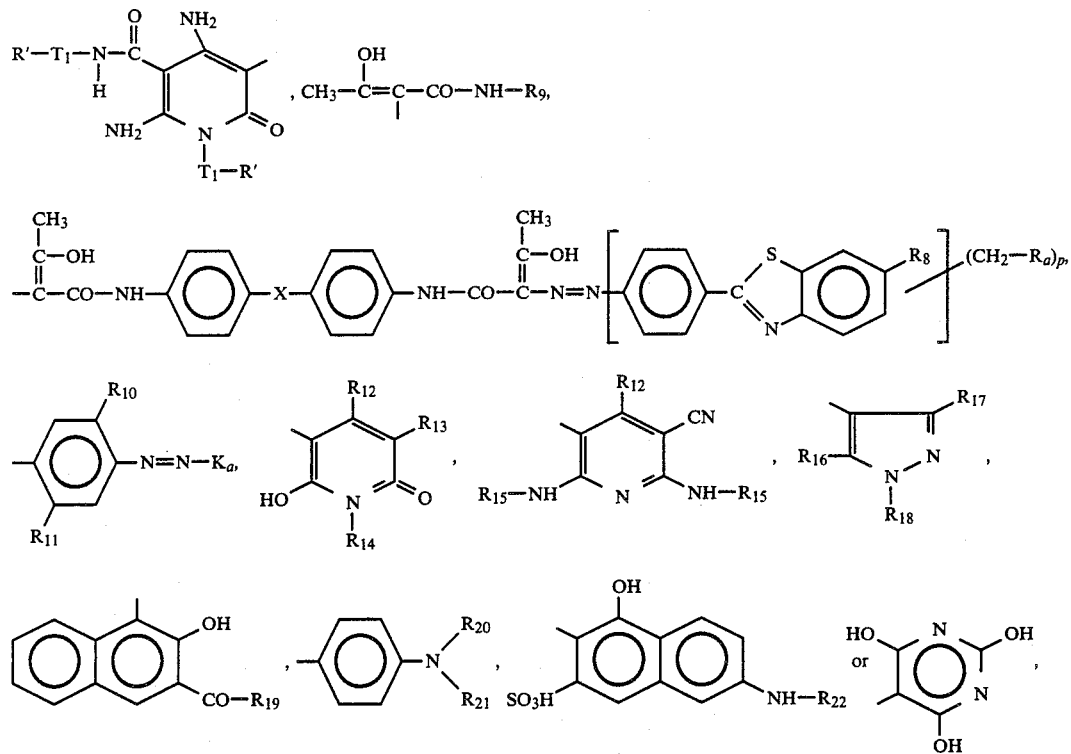
wherein $K_a$ is
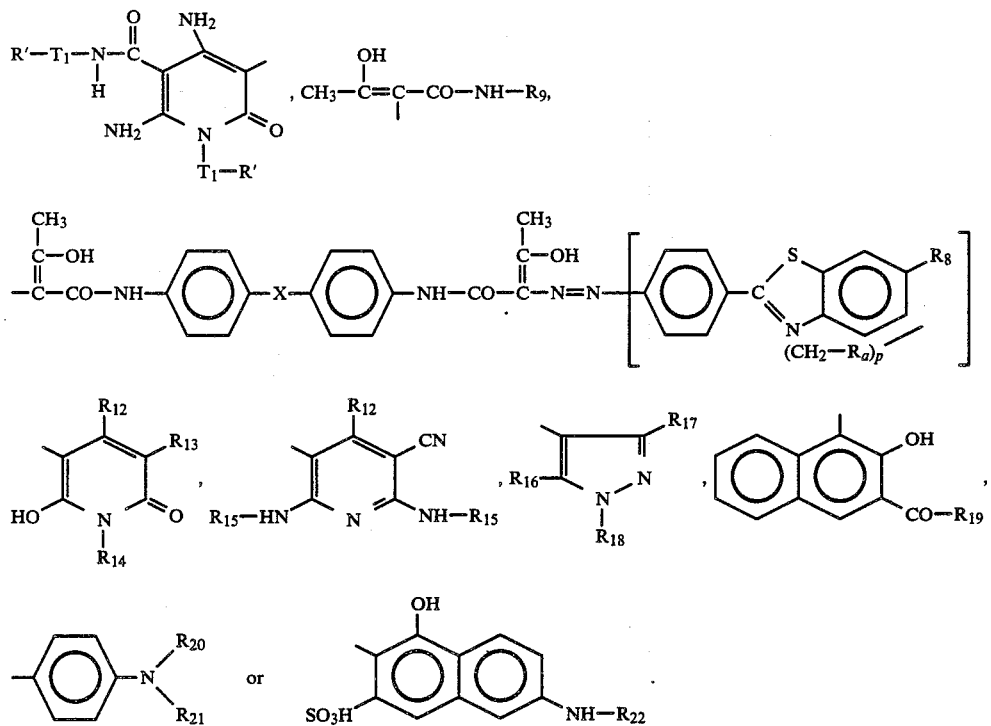
wherein
each R' and $T_1$ is as defined above, and
each $R_a$, $R_8$, $R_9$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, X and p is as defined below,
each $R_a$ is $-N(R_1')_2$ or $-N^\oplus(R_2')_3 A^\ominus$,
$R_8$ is hydrogen, methyl, methoxy or ethoxy,

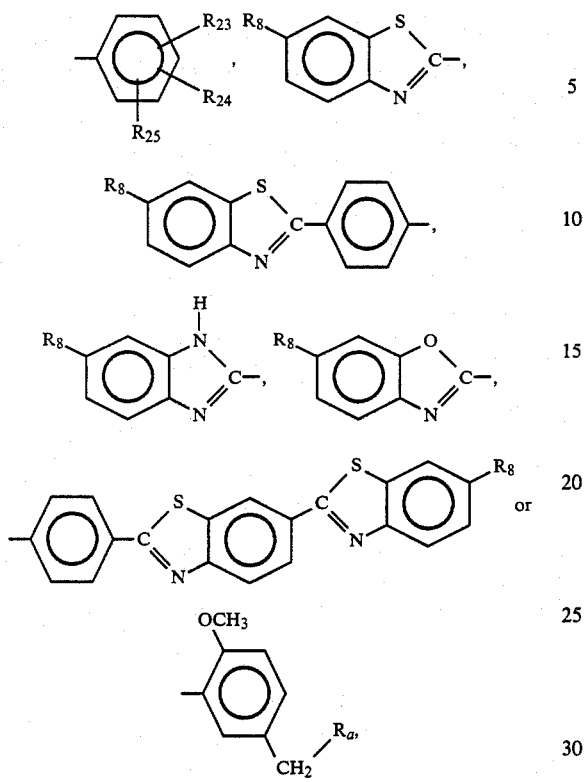

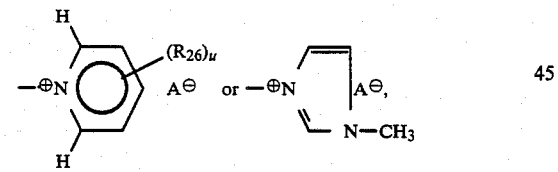

wherein
each of $R_{23}$, $R_{24}$ and $R_{25}$ is independently hydrogen, halo, $C_{1-4}$alkyl, $C_{1-4}$alkoxy, nitro or cyano, and
$R_a$ and $R_8$ are as defined above,
$R_{10}$ is $C_{1-4}$alkyl or $C_{1-4}$alkoxy,
$R_{11}$ is $C_{1-4}$alkyl or $C_{1-4}$alkoxy,
$R_{12}$ is hydrogen, $C_{1-4}$alkyl, benzyl or phenyl,
$R_{13}$ is hydrogen, cyano, carbamoyl,

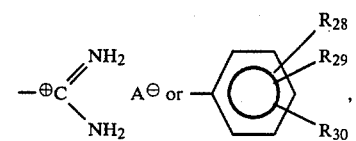

wherein
$R_{26}$ is $C_{1-4}$alkyl, amino, $C_{1-4}$alkylamino, di-($C_{1-4}$alkyl)amino, ($C_{1-4}$alkyl)carbamoyl or di-($C_{1-4}$alkyl)carbamoyl, and
u is 0, 1 or 2,
$R_{14}$ is hydrogen, $C_{1-4}$alkyl, phenyl($C_{1-4}$alkyl), 2-cyanoethyl, 2-hydroxyethyl, $-(CH_2)_r-N(R_{1a})_2$, 3-methoxypropyl, $-(CH_2)_r-N^{\oplus}(R_2')_3 A^{\ominus}$ or phenylamino, wherein
each $R_{1a}$ is $C_{1-12}$alkyl; $C_{1-12}$alkyl substituted by halo, cyano, hydroxy, phenyl or carbamoyl; cyclohexyl; cyclohexyl substituted by 1 to 3 $C_{1-4}$alkyl groups; phenyl or phenyl substituted by 1 to 3 $C_{1-4}$alkyl groups or
$-N(R_{1a})_2$ is piperidino, morpholino, piperazino, N'-$C_{1-4}$alkylpiperazino or pyrrolidino, and
r is 2, 3, 4, 5 or 6,
each $R_{15}$ is independently hydrogen, $C_{1-4}$alkyl, 3-methoxypropyl, 2-hydroxyethyl, 3-dimethylaminopropyl, 3-diethylaminopropyl or 3-trimethylammoniumpropyl $A^{\ominus}$,
$R_{16}$ is hydroxy or amino,
$R_{17}$ is $C_{1-4}$alkyl, $-CO-OR_{32}$ or $-CO-NR_{33}R_{34}$, wherein
$R_{32}$ is $C_{1-4}$alkyl,
$R_{33}$ is hydrogen or $C_{1-4}$alkyl, and
$R_{34}$ is hydrogen or $C_{1-4}$alkyl,
$R_{18}$ is

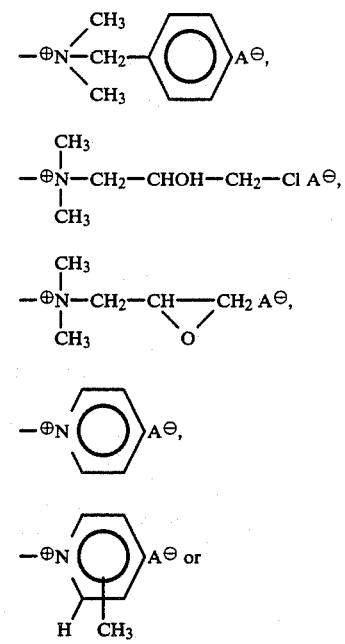

wherein
each of $R_{28}$ and $R_{29}$ is independently hydrogen, halo, $C_{1-4}$alkyl, $C_{1-4}$alkoxy, nitro, amino or acetamido, and
$R_{30}$ is hydrogen or $-NH-CO-(CH_2)_m-R_{35}$, wherein $R_{35}$ is $-N^{\oplus}(R_2')_3 A^{\ominus}$,

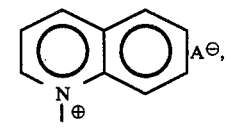

$R_{19}$ is hydrazino, $-NH-(CH_2)_m-N(R_1')_2$ or nitrophenylamino,
$R_{20}$ is $C_{1-4}$alkyl, benzyl or 2-cyanoethyl,
$R_{21}$ is $C_{1-4}$alkyl, $-(CH_2)_m-N^{\oplus}(CH_3)_3 A^{\ominus}$ or

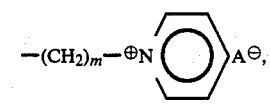

$R_{22}$ is 4,634,764
47
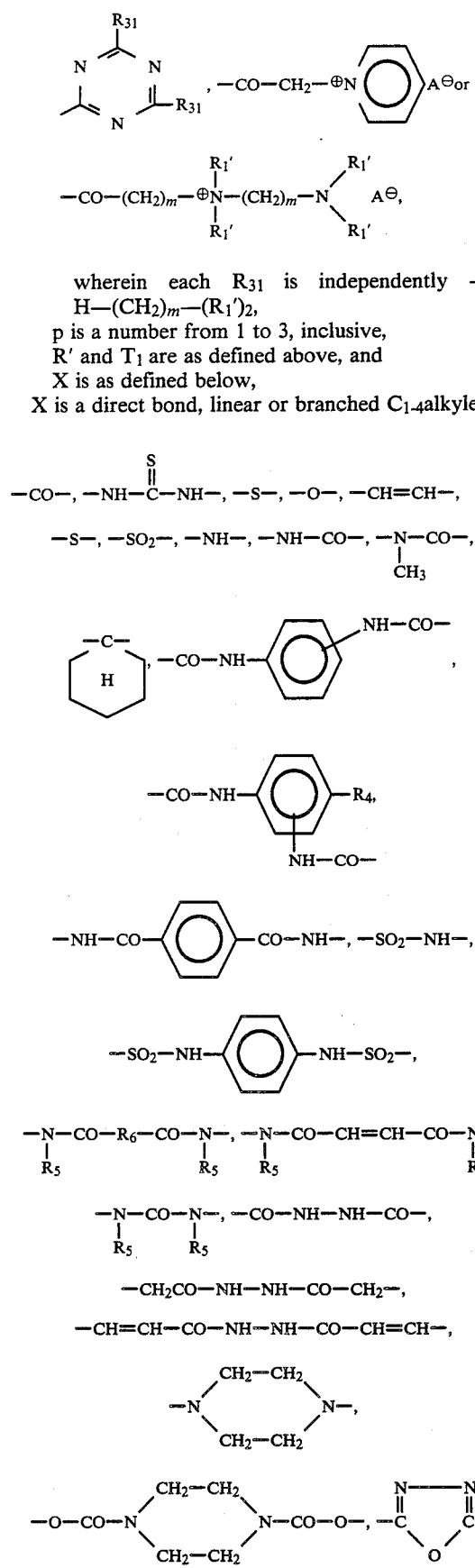
wherein each R₃₁ is independently —NH—(CH₂)ₘ—(R₁')₂,
p is a number from 1 to 3, inclusive,
R' and T₁ are as defined above, and
X is as defined below,
X is a direct bond, linear or branched C₁₋₄alkylene,
48
-continued
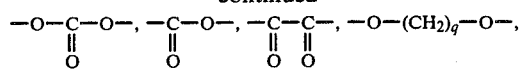
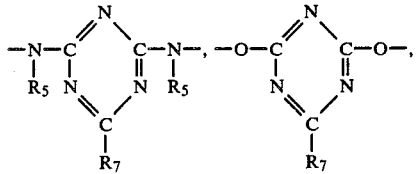
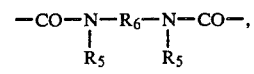
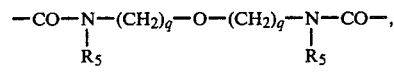
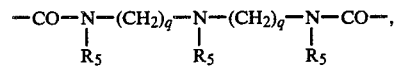
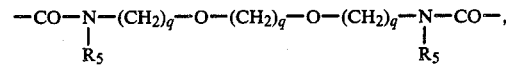
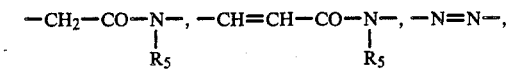
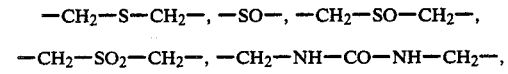
—CH₂—S—CH₂—, —SO—, —CH₂—SO—CH₂—,
—CH₂—SO₂—CH₂—, —CH₂—NH—CO—NH—CH₂—,
—CH₂—NH—CS—NH—CH₂—,
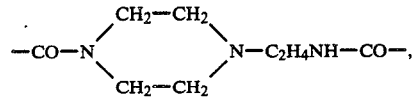
—CH₂—CH₂—CO—N—, —CH₂—CO—CH₂—,
                    |
                    R₅
—CH=CH—CH=CH—,
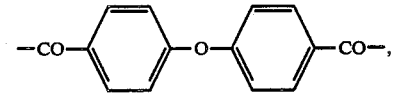
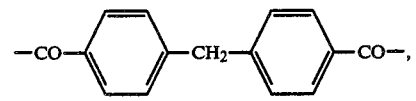
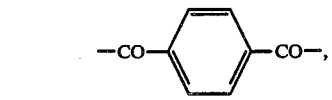
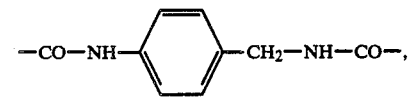
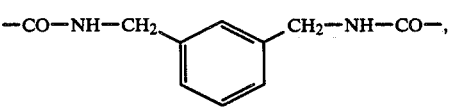

-continued

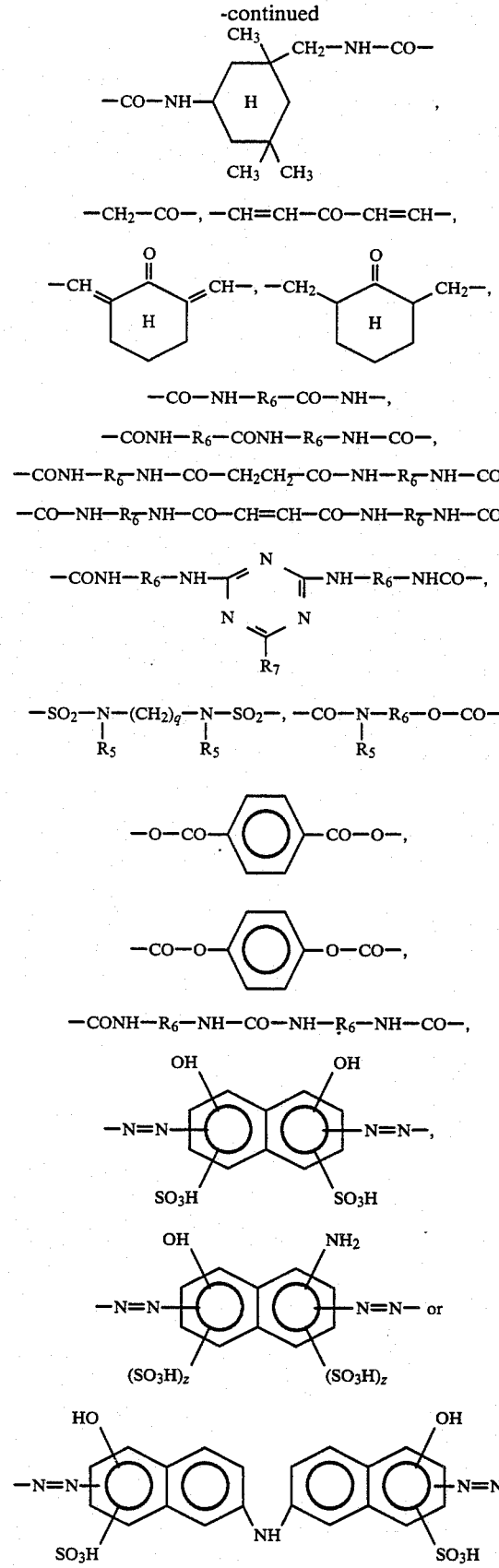

wherein
$R_4$ is halo, $C_{1-4}$alkyl or $C_{1-4}$alkoxy, each $R_5$ is independently hydrogen or $C_{1-4}$alkyl,
each $R_6$ is independently linear or branched $C_{1-4}$alkylene,
$R_7$ is hydroxy, halo, amino, dimethylamino, diethylamino, 2-hydroxyethylamino, di-(2-hydroxyethyl)amino, 3-dimethylaminopropylamino, 3-diethylaminopropylamino, N-methyl-N-phenylamino or N-cyclohexyl-N-methylamino,
each q is independently 1, 2, 3 or 4, and
each z is independently 0, 1 or 2,
with the proviso that when at least one $R_3$ is other than hydrogen, X is a direct bond, linear or branched $C_{1-4}$alkylene,

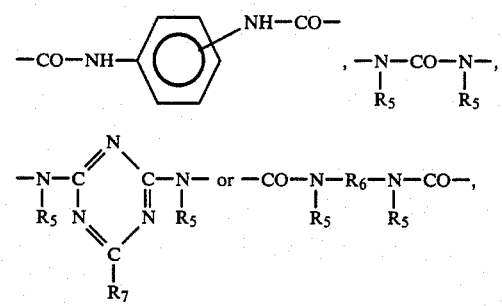

wherein $R_5$, $R_6$ and $R_7$ are as defined above, wherein
each $A^\ominus$ is a non-chromophoric anion,
each m is independently 1, 2, 3, 4, 5 or 6, and
each $R_1'$ and $R_2'$ is as defined above.

5. A compound according to claim 4 wherein Z' is

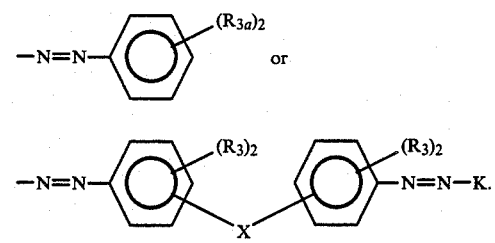

6. A compound according to claim 4 wherein Z' is hydrogen.

7. A compound according to claim 4 having the formula

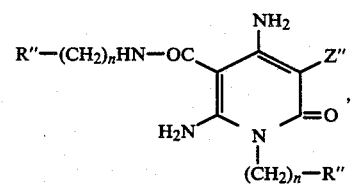

wherein
each R'' is hydroxy or $-N(R_1'')_2$,
wherein each $R_1''$ is hydrogen or $C_{1-4}$alkyl, Z'' is hydrogen,

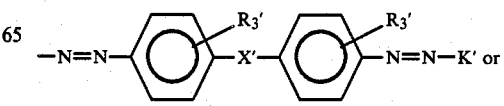

-continued
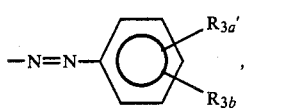
wherein
$R_{3a'}$ is hydrogen, chloro, nitro, phenylazo, 3-methylphenylazo, phenoxy, 4-chlorophenoxy or 3-methoxyphenoxy,
$R_{3b}$ is hydrogen, chloro, nitro or methyl, and
K' and X' are as defined below, and
each n is 2, 3, 4, 5 or 6,
wherein
K' is
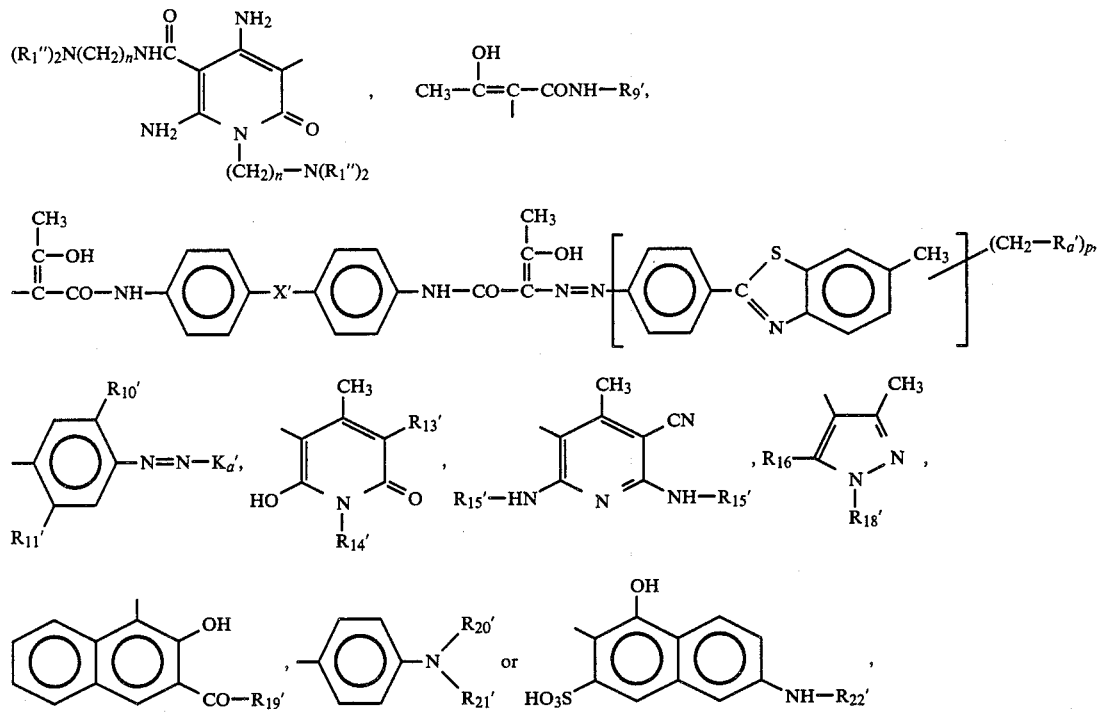
each $R_3'$ is independently hydrogen, methyl, methoxy or chloro,
wherein $K_a'$ is
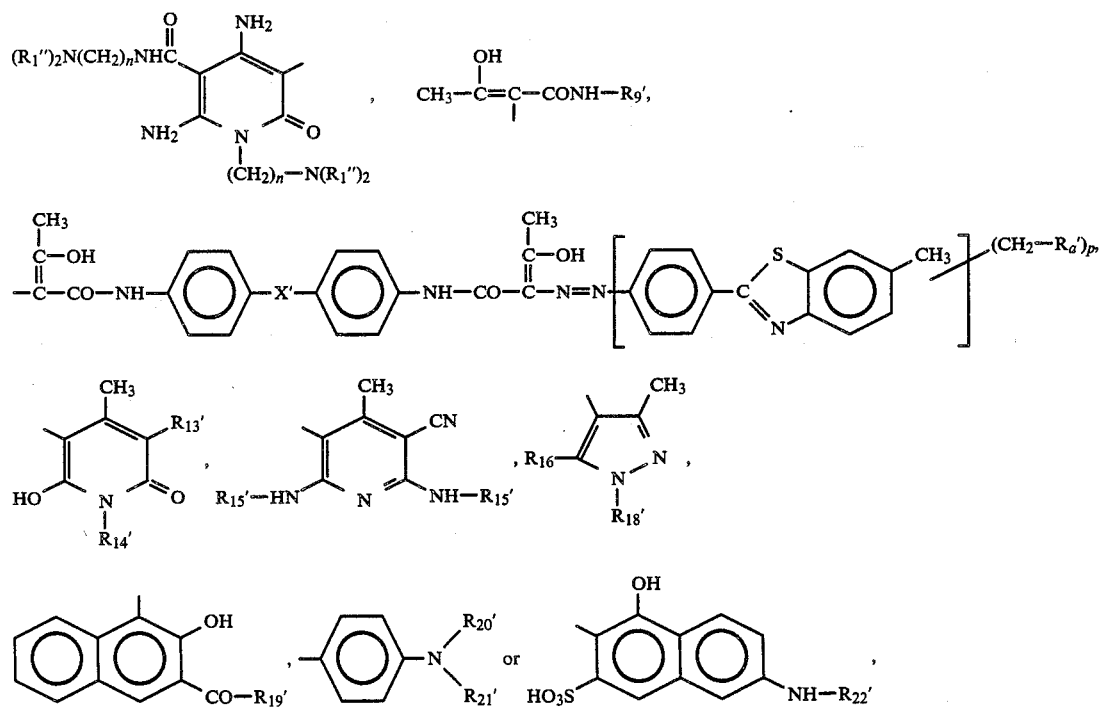

wherein
$R_a'$, $R_9'$, $R_{13}'$, $R_{14}'$, $R_{15}'$, $R_{16}$, $R_{18}'$, $R_{19}'$, $R_{20}'$, $R_{21}'$, $R_{22}'$, $X'$ and p are as defined below, and
each n is 2, 3, 4, 5 or 6,
each $R_a'$ is —N($R_1''$)$_2$ or —N$^\oplus$($R_2''$)$_2 R_{2b}'$ A$^\ominus$,
wherein
each $R_2''$ is independently $C_{1-4}$alkyl, and $R_{2b}'$ is methyl, ethyl or benzyl,
$R_9'$ is

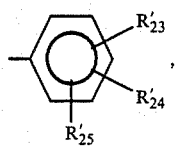,

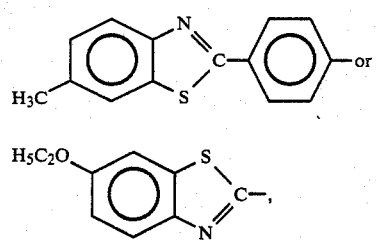

wherein each of $R_{23}'$, $R_{24}'$ and $R_{25}'$ is independently hydrogen, chloro, methyl, ethyl, methoxy or ethoxy,
$R_{10}'$ is methyl, ethyl, methoxy or ethoxy,
$R_{11}'$ is methyl, ethyl, methoxy or ethoxy,
$R_{13}'$ is hydrogen, cyano, carbamoyl, pyridinium A$^\ominus$, 3-methylpyridinium A$^\ominus$, 3-diethylcarbamoylpyridinium A$^\ominus$, 4-dimethylaminopyridinium A$^\ominus$ or

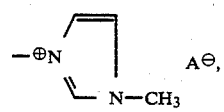

$R_{14}'$ is hydrogen, methyl, ethyl, benzyl, 2-phenylethyl, phenylamino, 2-hydroxyethyl, 3-methoxypropyl, 2-cyanoethyl, 3-dimethylaminopropyl, 3-trimethylammoniumpropyl A$^\ominus$ or 3-(N-benzyl-N,N-dimethylammonium)propyl A$^\ominus$,
each $R_{15}'$ is independently 2-hydroxyethyl, 3-methoxypropyl, 3-dimethylaminopropyl or 3-diethylaminopropyl,
$R_{16}$ is hydroxy or amino,
$R_{18}'$ is phenyl,

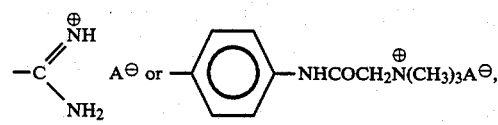

$R_{19}'$ is —NH—(CH$_2$)$_3$—N($R_1''$)$_2$ or 4-nitrophenylamino,
$R_{20}'$ is methyl, ethyl or benzyl,
$R_{21}'$ is methyl, ethyl, 2-trimethylammoniummethyl A$^\ominus$ or 2-pyridiniummethyl A$^\ominus$,
$R_{22}'$ is

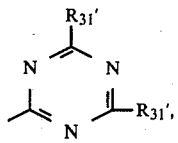

wherein
each $R_{31}'$ is —NH—(CH$_2$)$_m$—N(CH$_3$)$_2$ or —NH—(CH$_2$)$_m$—N(C$_2$H$_5$)$_2$, wherein m is 1, 2, 3, 4, 5 or 6,
n is 2, 3, 4, 5, 6,
p is a number from 1 to 3, inclusive, and
$X'$ is as defined below, and
$X'$ is a direct bond, —CH$_2$—, —(CH$_2$)$_2$—, —(CH$_2$)$_3$—, —(CH$_2$)$_4$—, —S—, —O—, —CH=CH—, —NH—, —NH—CO—,

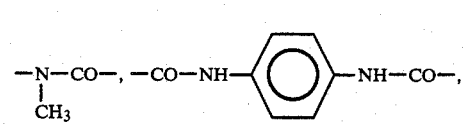

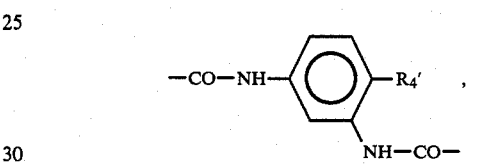

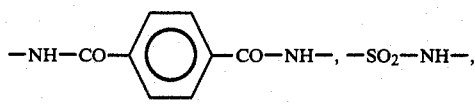

—NH—CO—CH$_2$CH$_2$—CO—NH—,

—NH—CO—(CH$_2$)$_4$—CO—NH—,

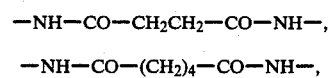

—NH—CO—CH=CH—CONH—,

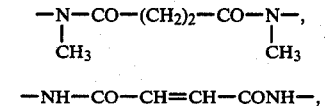

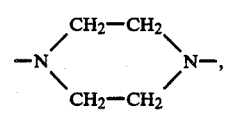

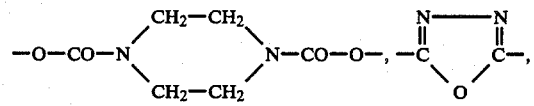

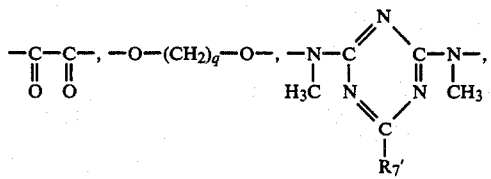

-continued

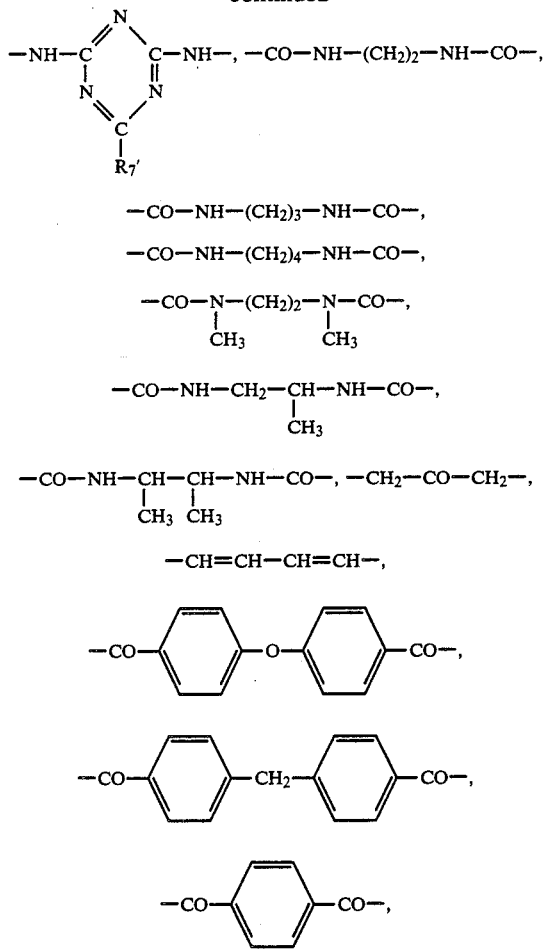

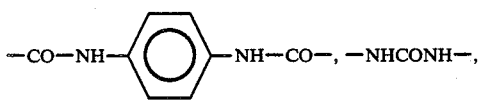

—CH₂—CO—, —CH=CH—CO—CH=CH— or
—CO—NH—R₆—CO—NH—, wherein
$R_4'$ is hydrogen, chloro, methyl or methoxy,
$R_6$ is linear or branched $C_{1-4}$alkylene,
$R_7'$ is hydroxy, chloro, amino, 2-hydroxyethylamino, di-(2-hydroxyethyl)amino, 3-diethylaminopropylamino, N-methyl-N-phenylamino or N-cyclohexyl-N-methylamino, and
q is 1, 2, 3 or 4,
with the proviso that when at least one $R_3'$ is other than hydrogen, X' is a direct bond, —CH₂—, —(CH₂)₂—,

—CO—NH—⌬—NH—CO—, —NHCONH—,

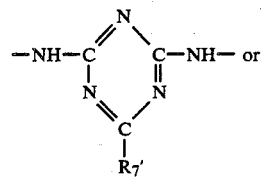

—CO—NH—(CH₂)₂—NH—CO—, wherein
each A⊖ is a non-chromophoric anion, and
each $R_1''$ is as defined above.

8. A compound according to claim 7 having the formula

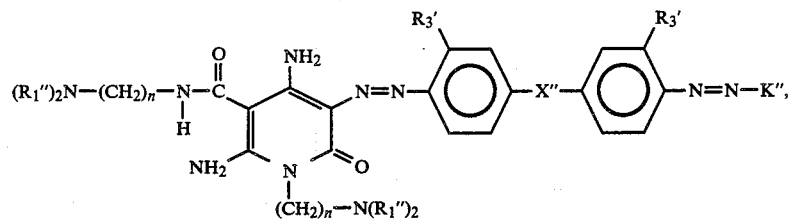

wherein
K" is

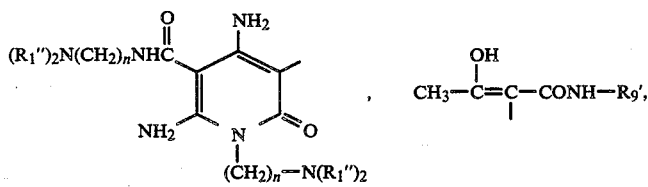 , 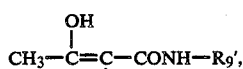

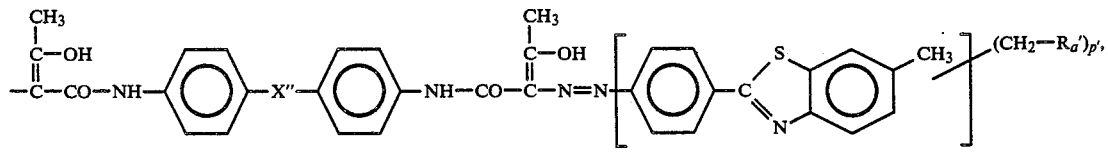

-continued

[chemical structures showing: phenylazo-Ka' with R10', R11'; pyridinone with CH3, R13', R14', HO; aminopyridine with CN, R15', R15'; pyrazole with CH3, R16, R18']

[chemical structures: naphthol with CO-R19'; phenyl-N(R20')(R21'); hydroxynaphthalene-SO3H with NH-R22']

wherein
p' is a number from 1 to 2,
$K_a'$, $R_a'$, $R_9'$, $R_{10}'$, $R_{11}'$, $R_{13}'$, $R_{14}'$, $R_{15}'$, $R_{16}$, $R_{18}'$, $R_{19}'$, $R_{20}'$, $R_{21}'$ and $R_{22}'$ are as defined in claim 7, and
$R_1''$, $X''$ and n are as defined below,
each $R_1''$ is hydrogen or $C_{1-4}$alkyl,
each $R_3'$ is independently hydrogen, methyl, methoxy or chloro,
$X''$ is a direct bond, $-CH_2-$, $-(CH_2)_2-$, $-NH-$, $-N(CH_3)-CO-$, $-CO-NH-C_6H_4-NH-CO-$, $-SO_2-NH-$, $-NH-CO-CH_2CH_2-CO-NH-$, $-NH-CO-(CH_2)_4-CO-NH-$, $-N(CH_3)-CO-(CH_2)_2-CO-N(CH_3)-$, $-NH-CO-CH=CH-CO-NH-$, $-N(CH_3)-CO-CH=CH-CO-N(CH_3)-$, $-NHCONH-$,

[heterocyclic structures: oxadiazole; triazine with H3C, CH3; triazine with R7']

$-NH-$[triazine-R7']$-NH-$, $-CO-NH-(CH_2)_2-NH-CO-$,

-continued $-CO-NH-(CH_2)_3-NH-CO-$, $-CO-NH-(CH_2)_4-NH-CO-$, $-CO-N(CH_3)-(CH_2)_2-N(CH_3)-CO-$, $-CO-NH-CH_2-CH(CH_3)-NH-CO-$, $-CO-NH-CH(CH_3)-CH(CH_3)-NH-CO-$, $-CO-C_6H_4-O-C_6H_4-CO-$, $-CO-C_6H_4-CH_2-C_6H_4-CO-$, $-CO-NH-C_6H_4-CH_2-NH-CO-$ or $-CO-NH-R_6-CO-NH-$, wherein
$R_6$ is a linear or branched $C_{1-4}$alkylene, and
$R_7'$ is hydroxy, chloro, amino, 2-hydroxyethylamino, di-(2-hydroxyethyl)amino, 3-diethylaminopropylamino, N-methyl-N-phenylamino or N-cyclohexyl-N-methylamino,
with the proviso that when at least one $R_3'$ is methyl, methoxy or chloro, $X''$ is a direct bond, and each n is 2, 3, 4, 5 or 6.

9. A compound according to claim 8 wherein each of $K''$ and $K_a'$ is other than

[chemical structure: $-C(CH_3)(OH)-C(CO-NH-C_6H_4-X''-C_6H_4-NH-CO-C(CH_3)(OH)-C-N=N-[C_6H_4-benzothiazole-CH_3]-(CH_2-R_a')_{p'}$]

10. The compound according to claim 7 having the formula

11. The compound according to claim 7 having the formula
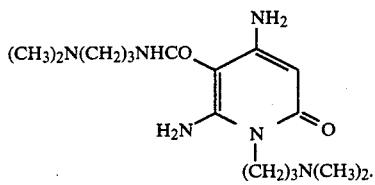
12. The compound according to claim 7 having the formula
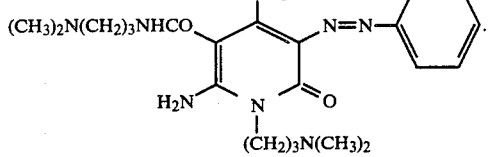
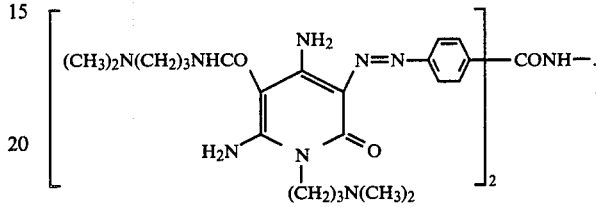
* * * * *